US010590174B2

(12) United States Patent
Gadea et al.

(10) Patent No.: US 10,590,174 B2
(45) Date of Patent: Mar. 17, 2020

(54) GENOMIC SEQUENCES ENCODING FOR AN ATTENUATED MUTANT ZIKA VIRUS

(71) Applicants: INSERM (INSTITUT NATIONAL DE LA SANTÉ ET DE LA RECHERCHE MÉDICALE), Paris (FR); UNIVERSITE DE LA REUNION SAINT DENIS, Saint Denis (FR); INSTITUT DE RECHERCHE POUR LE DÉVELOPPEMENT (IRD), Marseilles (FR); CENTRE NATIONAL DE LA RECHERCHE SCIENTIFIQUE (CNRS), Paris (FR)

(72) Inventors: Gilles Gadea, La Réunion (FR); Michael Girardot, Castelnau-le-Lez (FR); Philippe Despres, La Réunion (FR)

(73) Assignees: INSERM (INSTITUT NATIONAL DE LA SANTÉ ET DE LA RECHERCHE MÉDICALE), Paris (FR); UNIVERSITE DE LA REUNION SAINT DENIS, St. Denis (FR); INSTITUT DE RECHERCHE POUR LE DÉVELOPPEMENT (IRD), Marseilles (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 16/311,913

(22) PCT Filed: Jul. 7, 2017

(86) PCT No.: PCT/EP2017/067059
§ 371 (c)(1),
(2) Date: Dec. 20, 2018

(87) PCT Pub. No.: WO2018/007575
PCT Pub. Date: Jan. 11, 2018

(65) Prior Publication Data
US 2019/0177373 A1 Jun. 13, 2019

(30) Foreign Application Priority Data

Jul. 8, 2016 (EP) .................................... 16305863

(51) Int. Cl.
C07K 7/00 (2006.01)
C12N 15/11 (2006.01)
A61K 39/00 (2006.01)
C07K 14/005 (2006.01)
C12N 7/00 (2006.01)

(52) U.S. Cl.
CPC .............. *C07K 14/005* (2013.01); *C12N 7/00* (2013.01); *C12N 15/111* (2013.01); *A61K 39/00* (2013.01); *A61K 2039/5254* (2013.01); *C12N 2310/141* (2013.01); *C12N 2320/30* (2013.01); *C12N 2770/24122* (2013.01); *C12N 2770/24134* (2013.01); *C12N 2770/24162* (2013.01); *C12N 2999/005* (2013.01); *Y02A 50/392* (2018.01)

(58) Field of Classification Search
None
See application file for complete search history.

(56) References Cited

PUBLICATIONS

Database EMBL [Online] Feb. 25, 2016 (Feb. 25, 2016), "Zika virus strain MR 766 polyprotein gene, complete cds.", XP002765351, retrieved from EBI accession No. EM_STD:KU720415 Database accession No. KU720415 sequence.
Weaver Scott C et al "Zika virus: History, emergence, biology, and prospects for control", Antiviral Research, Elsevier BV, NL, vol. 130, Mar. 18, 2016, pp. 69-80.
Victor Satler Pylro et al: "ZIKV-CDB: A Collaborative Database to Guide Research Linking SncRNAs and Zika Virus Disease Symptoms", PLOS Neglected Tropical Diseases, vol. 10, No. 6, Jun. 22, 2016, p. e0004817.
Pylro V.S. et al: "hsa-miR-4279", ZIKV Collaborative Database, XP002765352, retrieved from Internet: URL:http://zikadb.cprr. fiocruz.br/zika/search_sncma.php?querry=4279 [retrieved on Dec. 16, 2016].
Anna Durbin: "Vaccine Development for Zika Virus—Timelines and Strategies", Seminars in Reproductive Medicine, vol. 34, No. 05, Sep. 8, 2016, pp. 299-304.
Amit Kumar Gupta et al: ZikaVR: An Integrated Zika Virus Resource for Genomics, Proteomics, Phylogenetic and Therapeutic Analysis, Scientific Reports, vol. 6, Sep. 16, 2016, p. 32713.
Konstantin A. Tsetsarkin et al: "A Full-Length Infectious cDNA Clone of Zika Virus from the 2015 Epidemic in Brazil as a Genetic Platform for Studies of Virus-Host Interations and Vaccine Development.", MBIO, vol. 7, No. 4, Aug. 23, 2016, pp. e01114-16.

*Primary Examiner* — Nicole Kinsey White
(74) *Attorney, Agent, or Firm* — W&C IP

(57) ABSTRACT

The present invention relates to a genomic sequences encoding for an attenuated mutant Zika virus. The inventors have introduced some specific substitutions at very specific positions in the epidemic genomic sequence for restoring some fixation sites for miR-4279 that were originally present in the endemic genomic sequence. Moreover the inventors have additionally introduced mutation leading to the abrogation of the N-glycosylation site on the E protein which will prevent the generation of auto-antibodies responsible for Guillain-Barre syndrome. The inventors have produced additional mutations of the virus that result to a dramatic reduction of the cytopathic effects without affecting the capacity to produce high titers of virus. In particular the present invention relates to a genomic sequence characterized by the sequence represented by SEQ ID NO:1 wherein at least one site of fixation for miR-4279 is restored.

13 Claims, 1 Drawing Sheet
Specification includes a Sequence Listing.

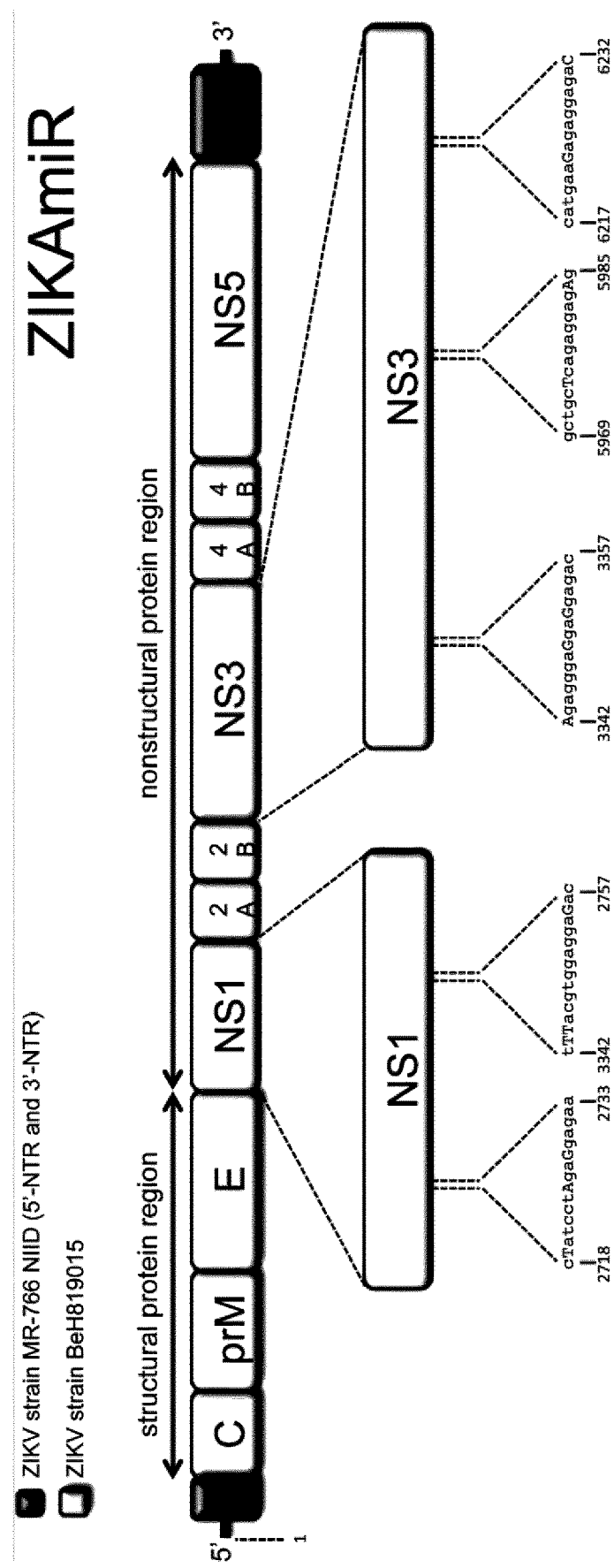

GENOMIC SEQUENCES ENCODING FOR AN ATTENUATED MUTANT ZIKA VIRUS

FIELD OF THE INVENTION

The present invention relates to a genomic sequences encoding for an attenuated mutant Zika virus.

BACKGROUND OF THE INVENTION

Zika virus is a mosquito-borne flavivirus that was first identified in Uganda in 1947 in monkeys through a network that monitored yellow fever. It was later identified in humans in 1952 in Uganda and the United Republic of Tanzania. Outbreaks of Zika virus disease have been recorded in Africa, the Americas, Asia and the Pacific. From the 1960s to 1980s, human infections were found across Africa and Asia, typically accompanied by mild illness. The first large outbreak of disease caused by Zika infection was reported from the Island of Yap (Federated States of Micronesia) in 2007. In July 2015 Brazil reported an association between Zika virus infection and Guillain-Barré syndrome. In October 2015 Brazil reported an association between Zika virus infection and microcephaly. Zika virus is primarily transmitted to people through the bite of an infected mosquito from the *Aedes* genus, mainly *Aedes aegypti* in tropical regions. *Aedes* mosquitoes usually bite during the day, peaking during early morning and late afternoon/evening. This is the same mosquito that transmits Zika virus, chikungunya and yellow fever. Sexual transmission of Zika virus is also possible. Other modes of transmission such as blood transfusion are being investigated. Zika virus disease is usually mild and requires no specific treatment. People sick with Zika virus should get plenty of rest, drink enough fluids, and treat pain and fever with common medicines. If symptoms worsen, they should seek medical care and advice. There is currently no vaccine available. WHO experts have suggested that the priority should be to develop attenuated vaccines and other non-live vaccines, which are safe to use in pregnant women and those of childbearing age.

SUMMARY OF THE INVENTION

The present invention relates to a genomic sequences encoding for an attenuated mutant Zika virus. In particular, the present invention is defined by the claims.

DETAILED DESCRIPTION OF THE INVENTION

The present invention relates to a genomic sequence encoding for an attenuated mutant Zika virus which provides the advantages of to be safe in particular for vaccinating pregnant women. In particular, the inventors have introduced some specific substitutions at very specific positions in the epidemic genomic sequence for restoring some fixation sites for miR-4279 that were originally present in the endemic genomic sequence. Moreover the inventors have additionally introduced mutation leading to the abrogation of the N-glycosylation site on the E protein which will prevent the generation of auto-antibodies responsible for Guillain-Barré syndrome. The inventors have produced additional mutations of the virus that result to a dramatic reduction of the cytopathic effects without affecting the capacity to produce high titers of virus.

Accordingly, the first object of the present invention relates to the genomic sequence of the epidemic strain wherein at least one site of fixation for miR-4279 is restored.

As used herein the term "Zika virus" has its general meaning in the art. The Zika virus is a positive sense single-stranded RNA molecule of 10794 bases long with two non-coding regions flanking regions known as the 5' NCR and the 3' NCR. The open reading frame of the Zika virus codes for a polyprotein that is subsequently cleaved into capsid (C), precursor membrane (prM), envelope (E), and non-structural proteins (NS). The E protein composes the majority of the virion surface and is involved with aspects of replication such as host cell binding and membrane fusion. NS1, NS3, and NS5 are large, highly-conserved proteins while the NS2A, NS2B, NS4A, and NS4B proteins are smaller, hydrophobic proteins. Located in the 3' NCR are 428 nucleotides that may play a part in translation, RNA packaging, cyclization, genome stabilization, and recognition. The 3' NCR forms a loop structure and the 5' NCR allows translation via a methylated nucleotide cap or a genome-linked protein.

The term "epidemic strain" refers to the Zika strain responsible for the epidemic infections. In particular, the epidemic strain is characterized by the genomic sequence represented by SEQ ID NO:1. In some embodiments, the epidemic Zika strain refers to the Zika strain BeH819015 (Genbank #KU365778).

As used herein, the term "miR" has its general meaning in the art and refers to the miRNA sequence publicly available from the database at the webpage for microma.sanger.ac.uk/sequences/ under the miRBase Accession number miR-4279, and is thus known per se.

In some embodiments, a first site of fixation is restored by substituting the adenosine (A) at position 2707 by a thymine (T), the guanine (G) a position 2713 by an adenosine (A), and the adenosine (A) at position 2716 by a guanine (G).

In some embodiments, a second site of fixation is restored by substituting the cytidine (C) at position 3331 by a thymine (T), the cytidine (C) at position 3332 by a thymine (T), and the cytidine (C) at position 3334 by a guanine (G).

In some embodiments, a third site of fixation is restored by substituting the guanine (G) at position 5106 by an adenosine (A), the adenosine (A) at position 5113 by a guanine (G), and the adenosine (A) at position 5116 by a guanine (G).

In some embodiments, a fourth site of fixation is restored by substituting the cytosine (C) at position 5962 by a thymine (T), and the guanine (G) at position 5971 by an adenosine (A).

In some embodiments, a fifth site of fixation is restored by substituting the adenosine (A) at position 6211 by a guanine (G), and the thymine (T) at position 6220 by a cytidine (C).

In some embodiments, 1, 2, 3, 4, or 5 sites of fixation are restored in the genomic sequence of the epidemic strain.

In some embodiments, the genomic sequence consists of the sequence represented by SEQ ID NO:2.

In some embodiments, the genomic sequence of the epidemic strain further comprises at least one mutation that leads to the abrogation of the N-glycosylation site on protein E. In some embodiments, the genomic sequence of the present invention encodes for a protein E wherein at least one amino acid residue at position 152, 156 or 158 is mutated. In some embodiments, the genomic sequence of the present invention encodes for a protein E wherein the isoleucine residue (I) at position 152 is substituted by a threonine residue (T). In some embodiments, the genomic sequence of the present invention encodes for a protein E wherein the threonine residue (T) at position 156 is substituted by an isoleucine residue (I). In some embodiments, the genomic sequence of the present invention encodes for a protein E wherein the histidine residue (H) is substituted by a tyrosine residue (Y). In some embodiments, the genomic sequence of the present invention encodes for a protein E wherein the isoleucine residue (I) at position 152 is substituted by a threonine residue (T), the threonine residue (T) at position 156 is substituted by an isoleucine residue (I), and the histidine residue (H) is substituted by a tyrosine residue (Y).

In some embodiments, the genomic sequence consists of the sequence represented by SEQ ID NO:3.

The genomic sequence of the present invention is particularly suitable for the production of an attenuated Zika virus. As used herein, the term "attenuated" has its general meaning in the art and in particular to a virus rendered less virulent. In particular the attenuated mutant Zika virus of the present invention is non-pathogenic. As used herein, the term "non-pathogenic" is used herein to mean non-virulent or unable to induce illness in particular Guillain-Barré syndrome.

Thus a further object of the present invention relates to an attenuated Zika virus encoding by the genomic sequence of the present invention.

In some embodiments, the attenuated mutant zika virus of the present invention is obtained by recombinant DNA technology wherein the genomic sequence of the present invention is cloned into standard protein expression vectors and used to infect appropriate host cells. The host cells are then cultured, thus expressing the desired virus, which can be purified to the desired extent and formulated into a suitable vaccine product.

Accordingly a further object of the present invention relates to a host cell comprising the genomic sequence of the present invention. The host cell is typically a cell line suitable for propagating the virus. Suitable cell lines include mammalian cells, such as Vero cells, AGMK cells, BHK-21 cells, COS-1 or COS-7 cells, MDCK cells, CV-1 cells, LLC-MK2 cells, primary cell lines such as foetal Rhesus lung (FRhL-2) cells, BSC-1 cells, and MRC-5 cells, or human diploid fibroblasts, as well as avian cells, chicken or duck embryo derived cell lines, e.g., AGE1 cells, and primary, chicken embryo fibroblasts, and mosquito cell lines, such as C6/36. The cultures are fed with medium capable of supporting growth of the cells. The host cells are maintained in culture for several days until the desired virus titer is achieved. Optionally, the cells are maintained in a continuous perfusion system from which virus can be intermittently or continuously obtained over the course of several days or more. Under non-continuous culture conditions, a virus titer of at least about $10^6$ to $10^7$ PFU/ml by 3-7 days post-infection, is desirable. To recover virus, the virus is harvested by common methods known in the art including slow-speed centrifugation, or by filtration. Methods for concentrating said virus(es) are within the scope of a person with ordinary skill in the art and include, for example, ultrafiltration, or precipitation with polyethelene glycol (PEG). Methods for purifying viruses are known to a person with ordinary skill in the art and typically include continuous or multi-step sucrose gradients, purification by column chromatography using size exclusion, ion exchange, adsorption, or affinity columns, or purification by partitioning in polymer two-phase or multi-phase systems, and any combination thereof. Methods for assaying for virus positive fractions include plaque assay, hemagglutination (HA) assay, and/or antigen assays such as immunoassays.

In some embodiments, the harvested attenuated mutant Zika virus of the present invention is rendered inactive. As used herein, the term "inactive" encompasses a virus that has been replicated, e.g., in vitro, and then killed using chemical or physical means such that it is no longer capable of replicating. For example, the live attenuated virus can be inactivated, using chemical agents, such as formaldehyde, betapropiolactone (BPL), or hydrogen peroxide, or using ultraviolet irradiation, or by using a combination of two or more inactivation steps (which can be the same or different, e.g., formaldehyde and BPL, formaldehyde and UV irradiation, BPL and UV irradiation, hydrogen peroxide and BPL, hydrogen peroxide and UV irradiation, etc., in any combination).

A further object of the present invention relates to vaccine composition comprising the attenuated Zika virus of the present invention.

As used herein the term "vaccine composition" is a composition suitable for administration to a human is capable of eliciting a specific immune response against a pathogen, such as Zika virus.

The vaccine composition of the present invention comprises an amount of live attenuated Zika virus of the present invention or an amount of inactive attenuated Zika virus of the present invention The vaccine composition of the present invention can also include one or more additional components capable of eliciting or enhancing an immune response, such as an excipient, carrier, and/or adjuvant. An "adjuvant" is an agent that enhances the production of an antigen-specific immune response as compared to administration of the antigen in the absence of the agent. Common adjuvants include aluminum containing adjuvants that include a suspension of minerals (or mineral salts, such as aluminum hydroxide, aluminum phosphate, aluminum hydroxyphosphate) onto which antigen is adsorbed. In the context of the present disclosure the adjuvants are aluminum-(alum-)free adjuvants, which are formulated in the absence of any such aluminum salts. Alum-free adjuvants include oil and water emulsions, such as water-in-oil, and oil-in-water (and variants thereof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components. Pharmaceutically acceptable carriers and excipients are well known and can be selected by those of skill in the art. For example, the carrier or excipient can favorably include a buffer. Optionally, the carrier or excipient also contains at least one component that stabilizes solubility and/or stability. Examples of solubilizing/stabilizing agents include detergents, for example, lauroyl sarcosine and/or polyoxyethethylene sorbitan monooleate. Alternative solubilizing/stabilizing agents include arginine, and glass forming polyols (such as sucrose, trehalose and the like). Numerous pharmaceutically acceptable carriers and/or pharmaceutically acceptable excipients are known in the art and are described, e.g., in Remington's Pharmaceutical Sciences, by E. W. Martin, Mack Publishing Co., Easton, Pa., 5th Edition (1975). Accordingly, suitable excipients and carriers can be selected by those of skill in the art to produce a formulation suitable for delivery to a subject by a selected route of administration. Suitable excipients include, without limitation: glycerol, Polyethylene glycol (PEG), Sorbitol, Trehalose, N-lauroylsarcosine sodium salt, L-proline, Non detergent sulfobetaine, Guanidine hydrochloride, Urea, Trimethylamine oxide, KCl, Cat2+, Mg2+, Mn2+, Zn2+ and other divalent cation related salts, Dithiothreitol, Dithioerytrol, and β-mercaptoethanol. Other excipients can be detergents (including: polyoxyethethylene sorbitan monooleate, Triton X-00, NP-40, Empigen BB, Octylglucoside, Lauroyl maltoside, Zwittergent 3-08, Zwittergent 3-0, Zwittergent 3-2, Zwittergent 3-4, Zwittergent 3-6, CHAPS, Sodium deoxycholate, Sodium dodecyl sulphate, Cetyltrimethylammonium bromide). Preparation of vaccine compositions, including those for administration to human subjects, is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757. Typically, the amount of antigen in each dose of the vaccine composition is selected as an amount which induces an immunoprotective response without significant, adverse side effects in the typical subject. Immunoprotective in this context does not necessarily mean completely protective against infection; it means protection against symptoms or disease, especially severe disease associated with the virus. The amount of antigen can vary depending upon which specific immunogen is employed. Generally, it is expected that each human dose will comprise 0.05-100 μg of inactivated virus, such as from about 0.1 μg (e.g., 0.1, 0.2, 0.3, 0.4, or 0.5 μg) to about 50 μg, for example, from about 0.5 μg to about 30 μg, such as about 1 μg, about 2 μg, about 3 μg, about 4 μg, about 5 μg, about 10 μg, about 15 μg, about 20 μg, or about 25 μg, of each strain of inactivated Zika virus. Typically, the vaccine composition is prepared as injectable, either as liquid solution or suspension; solid form suitable for solution in, or suspension in, liquid prior to injection may also be prepared.

A further object of the present invention relates to a method for eliciting an immune response against Zika virus in a subject comprising administering to the subject a therapeutically effective amount of the vaccine composition of the present invention.

In some embodiments, the vaccine composition of the present invention is administered to adult or infant humans. In some embodiments, the vaccine composition of the present invention is administered to a pregnant woman. In some embodiments, the vaccine composition of the present invention is administered to a woman of childbearing age. In some embodiments, the subject was previously exposed to Zika virus.

In some embodiments, the vaccine composition of the present invention is particularly suitable for the prevention, amelioration or treatment of Zika virus infection and/or Zika virus induced disease.

Although the vaccine composition can be administered by a variety of different routes, most commonly, the vaccine composition is delivered by an intramuscular, subcutaneous or intradermal route of administration. Generally, the vaccine composition may be administered subcutaneously, intradermally, or intramuscularly in a dose effective for the production of neutralizing antibody and protection. The vaccines are administered in a manner compatible with the dosage formulation, and in such amount as will be prophylactically and/or therapeutically effective. The quantity to be administered, which is generally in the range of 0.05-100 μg of virus per dose, depends on the subject to be treated, capacity of the subject's immune system to synthesize antibodies, and the degree of protection desired. Precise amounts of the vaccine to be administered may depend on the judgment of the practitioner and may be peculiar to each subject.

The vaccine composition may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months or years. The dosage regimen will also, at least in part, be determined by the need of the subject and be dependent upon the judgment of the practitioner. Examples of suitable immunization schedules include: a first dose, followed by a second dose between 7 days and 6 months, and an optional third dose between 1 month and two years post initial immunization, or other schedules sufficient to elicit titers of virus-neutralizing antibodies expected to confer protective immunity. The generation of protective immunity against Zika virus with the vaccine composition may reasonably be expected after a primary course of immunization consisting of 1 to 3 inoculations. These could be supplemented by boosters at intervals (e.g., every two years) designed to maintain a satisfactory level of protective immunity.

The invention will be further illustrated by the following figures and examples. However, these examples and figures should not be interpreted in any way as limiting the scope of the present invention.

FIGURES

FIG. 1 shows the details of the clone ZIKAmir.

EXAMPLE

We have introduced some substitutions at very specific positions in the epidemic genomic sequence for restoring some fixation sites for miR-4279 that were originally present in the endemic genomic sequence (FIG. 1). The clone (named "ZIKAmir") was then compared to the epidemic clone in a progeny production assay. Briefly, Vero cells ($10^e5$/well) were seeded in 48-well culture plates. Tenfold serial dilutions of virus samples were prepared in duplicate in culture medium supplemented with 5% heat-inactivated FBS and 0.1 mL of each dilution was added to the cells. The plates were incubated for 2h at 37° C. 0.1 ml of culture medium supplemented with 0.8% carboxymethylcellulose (CMC) was added to each well, followed by an incubation at 37° C. for 4 days. The CMC overlay was removed and the cells were first fixed with 3.7% PFA for 10 min and then stained with 0.5% crystal violet in 20% ethanol. Plaques were counted and expressed as plaque-forming units per mL ($PFU \cdot mL^{-1}$). As shown in Table 1, the progeny production is decreased in comparison to the production observed with the epidemic and endemic virus.

TABLE 1

Progeny ZIKV production on Vero cells (passage 2) (log PFU · mL$^{-1}$) of the different clones

| molecular clones of Zika virus | Virus progeny production on Vero cells, passage 2 (log PFU · mL$^{-1}$) |
|---|---|
| BeH819015$^{MC}$ (strain Brazil 2015) | 7.0 |
| BeH819015$^{MC}$-mutant MiR4279 | 6.0 |

Sequences:

```
SEQ ID NO: 1: Genomic sequence of parental ZIKVBR15-MC
BeH819015 (10,727 nt)
TGTGAATCAGACTGCGACAGTTCGAGTTTGAAGCGAAAGCTAGCAACAGT

ATCAACAGGTTTTATTTTGGATTTGGAAACGAGAGTTTCTGGTCATGAAAAACCC

AAAAAAGAAATCCGGAGGATTCCGGATTGTCAATATGCTAAAACGCGGAGTAGC

CCGTGTGAGCCCCTTTGGGGGCTTGAAGAGGCTGCCAGCCGGACTTCTGCTGGGT

CATGGGCCCATCAGGATGGTCTTGGCGATTCTAGCCTTTTTGAGATTCACGGCAA

TCAAGCCATCACTGGGTCTCATCAATAGATGGGGTTCAGTTGGGAAAAAAGAGG

CTATGGAAATAATAAAGAAGTTCAAGAAAGATCTGGCTGCCATGCTGAGAATAA

TCAATGCTAGGAAGGAGAAGAAGAGACGAGGCGCAGATACTAGTGTCGGAATTG

TTGGCCTCCTGCTGACCACAGCTATGGCAGCGGAGGTCACTAGACGTGGGAGTGC

ATACTATATGTACTTGGACAGAAACGATGCTGGGGAGGCCATATCTTTTCCAACC

ACATTGGGGATGAATAAGTGTTATATACAGATCATGGATCTTGGACACATGTGTG

ATGCCACCATGAGCTATGAATGCCCTATGCTGGATGAGGGGGTGGAACCAGATG

ACGTCGATTGTTGGTGCAACACGACGTCAACTTGGGTTGTGTACGGAACCTGCCA

TCACAAAAAAGGTGAAGCACGGAGATCTAGAAGAGCTGTGACGCTCCCCTCCCA

TTCCACTAGGAAGCTGCAAACGCGGTCGCAAACCTGGTTGGAATCAAGAGAATA

CACAAAGCACTTGATTAGAGTCGAAAATTGGATATTCAGGAACCCTGGCTTCGCG

TTAGCAGCAGCTGCCATCGCTTGGCTTTTGGGAAGCTCAACGAGCCAAAAAGTCA

TATACTTGGTCATGATACTGCTGATTGCCCCGGCATACAGCATCAGGTGCATAGG

AGTCAGCAATAGGGACTTTGTGGAAGGTATGTCAGGTGGGACTTGGGTTGATGTT

GTCTTGGAACATGGAGGTTGTGTCACCGTAATGGCACAGGACAAACCGACTGTCG

ACATAGAGCTGGTTACAACAACAGTCAGCAACATGGCGGAGGTAAGATCCTACT

GCTATGAGGCATCAATATCAGACATGGCTTCGGACAGCCGCTGCCCAACACAAG

GTGAAGCCTACCTTGACAAGCAATCAGACACTCAATATGTCTGCAAAAGAACGTT

AGTGGACAGAGGCTGGGGAAATGGATGTGGACTTTTTGGCAAAGGGAGCCTGGT

GACATGCGCTAAGTTTGCATGCTCCAAGAAAATGACCGGGAAGAGCATCCAGCC

AGAGAATCTGGAGTACCGGATAATGCTGTCAGTTCATGGCTCCCAGCACAGTGGG

ATGATCGTTAATGACACAGGACATGAAACTGATGAGAATAGAGCGAAAGTTGAG

ATAACGCCCAATTCACCAAGAGCCGAAGCCACCCTGGGGGGTTTTGGAAGCCTA

GGACTTGATTGTGAACCGAGGACAGGCCTTGACTTTTCAGATTTGTATTACTTGAC

TATGAATAACAAGCACTGGTTGGTTCACAAGGAGTGGTTCCACGACATTCCATTA

CCTTGGCACGCTGGGGCAGACACCGGAACTCCACACTGGAACAACAAAGAAGCA

CTGGTAGAGTTCAAGGACGCACATGCCAAAAGGCAAACTGTCGTGGTTCTAGGG

AGTCAAGAAGGAGCAGTTCACACGGCCCTTGCTGGAGCTCTGGAGGCTGAGATG

GATGGTGCAAAGGGAAGGCTGTCCTCTGGCCACTTGAAATGTCGCCTGAAAATGG

ATAAACTTAGATTGAAGGGCGTGTCATACTCCTTGTGTACTGCAGCGTTCACATTC

ACCAAGATCCCGGCTGAAACACTGCACGGGACAGTCACAGTGGAGGTACAGTAC

GCAGGGACAGATGGACCTTGCAAGGTTCCAGCTCAGATGGCGGTGGACATGCAA

ACTCTGACCCCAGTTGGGAGGTTGATAACCGCTAACCCCGTAATCACTGAAAGCA

CTGAGAACTCTAAGATGATGCTGGAACTTGATCCACCATTTGGGGACTCTTACAT
```

-continued

```
TGTCATAGGAGTCGGGGAGAAGAAGATCACCCACCACTGGCACAGGAGTGGCAG
CACCATTGGAAAAGCATTTGAAGCCACTGTGAGAGGTGCCAAGAGAATGGCAGT
CTTGGGAGACACAGCCTGGGACTTTGGATCAGTTGGAGGCGCTCTCAACTCATTG
GGCAAGGGCATCCATCAAATTTTTGGAGCAGCTTTCAAATCATTGTTTGGAGGAA
TGTCCTGGTTCTCACAAATTCTCATTGGAACGTTGCTGATGTGGTTGGGTCTGAAC
ACAAAGAATGGATCTATTTCCCTTATGTGCTTGGCCTTAGGGGGGGTGTTGATCTT
CTTATCCACAGCCGTCTCTGCTGATGTGGGGTGCTCGGTGGACTTCTCAAAGAAG
GAGACGAGATGCGGTACAGGGGTGTTCGTCTATAACGACGTTGAAGCCTGGAGG
GACAGGTACAAGTACCATCCTGACTCCCCCCGTAGATTGGCAGCAGCAGTCAAGC
AAGCCTGGGAAGATGGTATCTGCGGGATCTCCTCTGTTTCAAGAATGGAAAACAT
CATGTGGAGATCAGTAGAAGGGGAGCTCAACGCAATCCTGGAAGAGAATGGAGT
TCAACTGACGGTCGTTGTGGGATCTGTAAAAAACCCCATGTGGAGAGGTCCACAG
AGATTGCCCGTGCCTGTGAACGAGCTGCCCCACGGCTGGAAGGCTTGGGGGAAA
TCGTACTTCGTCAGAGCAGCAAAGACAAATAACAGCTTTGTCGTGGATGGTGACA
CACTGAAGGAATGCCCACTCAAACATAGAGCATGGAACAGCTTTCTTGTGGAGG
ATCATGGGTTCGGGTATTTCACACTAGTGTCTGGCTCAAGGTTAGAGAAGATTA
TTCATTAGAGTGTGATCCAGCCGTTATTGGAACAGCTGTTAAGGGAAAGGAGGCT
GTACACAGTGATCTAGGCTACTGGATTGAGAGTGAGAAGAATGACACATGGAGG
CTGAAGAGGGCCCATCTGATCGAGATGAAAACATGTGAATGGCCAAAGTCCCAC
ACATTGTGGACAGATGGAATAGAAGAGAGTGATCTGATCATACCCAAGTCTTTAG
CTGGGCCACTCAGCCATCACAATACCAGAGAGGGCTACAGGACCCAAATGAAAG
GGCCATGGCACAGTGAAGAGCTTGAAATTCGGTTTGAGGAATGCCCAGGCACTA
AGGTCCACGTGGAGGAAACATGTGGAACAAGAGGACCATCTCTGAGATCAACCA
CTGCAAGCGGAAGGGTGATCGAGGAATGGTGCTGCAGGGAGTGCACAATGCCCC
CACTGTCGTTCCGGGCTAAAGATGGCTGTTGGTATGGAATGGAGATAAGGCCCAG
GAAAGAACCAGAAAGCAACTTAGTAAGGTCAATGGTGACTGCAGGATCAACTGA
TCACATGGACCACTTCTCCCTTGGAGTGCTTGTGATCCTGCTCATGGTGCAGGAA
GGGCTGAAGAAGAGAATGACCACAAAGATCATCATAAGCACATCAATGGCAGTG
CTGGTAGCTATGATCCTGGGAGGATTTTCAATGAGTGACCTGGCTAAGCTTGCAA
TTTTGATGGGTGCCACCTTCGCGGAAATGAACACTGGAGGAGATGTAGCTCATCT
GGCGCTGATAGCGGCATTCAAAGTCAGACCAGCGTTGCTGGTATCTTTCATCTTC
AGAGCTAATTGGACACCCCGTGAAAGCATGCTGCTGGCCTTGGCCTCGTGTCTTT
TGCAAACTGCGATCTCCGCCTTGGAAGGCGACCTGATGGTTCTCATCAATGGTTTT
GCTTTGGCCTGGTTGGCAATACGAGCGATGGTTGTTCCACGCACTGATAACATCA
CCTTGGCAATCCTGGCTGCTCTGACACCACTGGCCCGGGGCACACTGCTTGTGGC
GTGGAGAGCAGGCCTTGCTACTTGCGGGGGGTTTATGCTCCTCTCTCTGAAGGGA
AAAGGCAGTGTGAAGAAGAACTTACCATTTGTCATGGCCCTGGGACTAACCGCTG
TGAGGCTGGTCGACCCCATCAACGTGGTGGGACTGCTGTTACTCACAAGGAGTGG
GAAGCGGAGCTGGCCCCCTAGCGAAGTACTCACAGCTGTTGGCCTGATATGCGCA
TTGGCTGGAGGGTTCGCCAAGGCAGATATAGAGATGGCTGGGCCCATGGCCGCG
GTCGGTCTGCTAATTGTCAGTTACGTGGTCTCAGGAAAGAGTGTGGACATGTACA
```

-continued

```
TTGAAAGAGCAGGTGACATCACATGGGAAAAAGATGCGGAAGTCACTGGAAACA
GTCCCCGGCTCGATGTGGCGCTAGATGAGAGTGGTGATTTCTCCCTGGTGGAGGA
TGACGGTCCCCCCATGAGAGAGATCATACTCAAGGTGGTCCTGATGACCATCTGT
GGCATGAATCCAATAGCCATACCCTTTGCAGCTGGAGCGTGGTACGTATACGTGA
AGACTGGAAAAAGGAGTGGTGCTCTATGGGATGTGCCTGCTCCCAAGGAAGTAA
AAAAGGGGGAGACCACAGATGGAGTGTACAGAGTAATGACTCGTAGACTGCTAG
GTTCAACACAAGTTGGAGTGGGAGTTATGCAAGAGGGGGTCTTTCACACTATGTG
GCACGTCACAAAAGGATCCGCGCTGAGAAGCGGTGAAGGGAGACTTGATCCATA
CTGGGGAGATGTCAAGCAGGATCTGGTGTCATACTGTGGTCCATGGAAGCTAGAT
GCCGCCTGGGACGGGCACAGCGAGGTGCAGCTCTTGGCCGTGCCCCCCGGAGAG
AGAGCGAGGAACATCCAGACTCTGCCCGGAATATTTAAGACAAAGGATGGGGAC
ATTGGAGCGGTTGCGCTGGATTACCCAGCAGGAACTTCAGGATCTCCAATCCTAG
ACAAGTGTGGGAGAGTGATAGGACTTTATGGCAATGGGGTCGTGATCAAAAATG
GGAGTTATGTTAGTGCCATCACCCAAGGGAGGAGGGAAGAAGAGACTCCTGTTG
AGTGCTTCGAGCCCTCGATGCTGAAGAAGAAGCAGCTAACTGTCTTAGACTTGCA
TCCTGGAGCTGGGAAAACCAGGAGAGTTCTTCCTGAAATAGTCCGTGAAGCCATA
AAAACAAGACTCCGTACTGTGATCTTAGCTCCAACCAGGGTTGTCGCTGCTGAAA
TGGAGGAGGCCCTTAGAGGGCTTCCAGTGCGTTATATGACAACAGCAGTCAATGT
CACCCACTCTGGAACAGAAATCGTCGACTTAATGTGCCATGCCACCTTCACTTCA
CGTCTACTACAGCCAATCAGAGTCCCCAACTATAATCTGTATATTATGGATGAGG
CCCACTTCACAGATCCCTCAAGTATAGCAGCAAGAGGATACATTTCAACAAGGGT
TGAGATGGGCGAGGCGGCTGCCATCTTCATGACCGCCACGCCACCAGGAACCCGT
GACGCATTTCCGGACTCCAACTCACCAATTATGGACACCGAAGTGGAAGTCCCAG
AGAGAGCCTGGAGCTCAGGCTTTGATTGGGTGACGGATCATTCTGGAAAAACAGT
TTGGTTTGTTCCAAGCGTGAGGAACGGCAATGAGATCGCAGCTTGTCTGACAAAG
GCTGGAAAACGGGTCATACAGCTCAGCAGAAAGACTTTTGAGACAGAGTTCCAG
AAAACAAAACATCAAGAGTGGGACTTTGTCGTGACAACTGACATTTCAGAGATG
GGCGCCAACTTTAAAGCTGACCGTGTCATAGATTCCAGGAGATGCCTAAAGCCGG
TCATACTTGATGGCGAGAGAGTCATTCTGGCTGGACCCATGCCTGTCACACATGC
CAGCGCTGCCCAGAGGAGGGGCGCATAGGCAGGAATCCCAACAAACCTGGAGA
TGAGTATCTGTATGGAGGTGGGTGCGCAGAGACTGACGAAGACCATGCACACTG
GCTTGAAGCAAGAATGCTCCTTGACAATATTTACCTCCAAGATGGCCTCATAGCC
TCGCTCTATCGACCTGAGGCCGACAAAGTAGCAGCCATTGAGGGAGAGTTCAAG
CTTAGGACGGAGCAAAGGAAGACCTTTGTGGAACTCATGAAAAGAGGAGATCTT
CCTGTTTGGCTGGCCTATCAGGTTGCATCTGCCGGAATAACCTACACAGATAGAA
GATGGTGCTTTGATGGCACGACCAACAACACCATAATGGAAGATAGTGTGCCGG
CAGAGGTGTGGACCAGACACGGAGAGAAAAGAGTGCTCAAACCGAGGTGGATG
GACGCCAGAGTTTGTTCAGATCATGCGGCCCTGAAGTCATTCAAGGAGTTTGCCG
CTGGGAAAAGAGGAGCGGCTTTTGGAGTGATGGAAGCCCTGGGAACACTGCCAG
GACACATGACAGAGAGATTCCAGGAAGCCATTGACAACCTCGCTGTGCTCATGCG
GGCAGAGACTGGAAGCAGGCCTTACAAAGCCGCGGCGGCCCAATTGCCGGAGAC
```

-continued

```
CCTAGAGACCATAATGCTTTTGGGGTTGCTGGGAACAGTCTCGCTGGGAATCTTC
TTCGTCTTGATGAGGAACAAGGGCATAGGGAAGATGGGCTTTGGAATGGTGACTC
TTGGGGCCAGCGCATGGCTCATGTGGCTCTCGGAAATTGAGCCAGCCAGAATTGC
ATGTGTCCTCATTGTTGTGTTCCTATTGCTGGTGGTGCTCATACCTGAGCCAGAAA
AGCAAAGATCTCCCCAGGACAACCAAATGGCAATCATCATCATGGTAGCAGTAG
GTCTTCTGGGCTTGATTACCGCCAATGAACTCGGATGGTTGGAGAGAACAAAGAG
TGACCTAAGCCATCTAATGGGAAGGAGAGAGGAGGGGGCAACCATAGGATTCTC
AATGGACATTGACCTGCGGCCAGCCTCAGCTTGGGCCATCTATGCTGCCTTGACA
ACTTTCATTACCCCAGCCGTCCAACATGCAGTGACCACCTCATACAACAACTACT
CCTTAATGGCGATGGCCACGCAAGCTGGAGTGTTGTTTGGTATGGGCAAAGGGAT
GCCATTCTACGCATGGGACTTTGGAGTCCCGCTGCTAATGATAGGTTGCTACTCA
CAATTAACACCCCTGACCCTAATAGTGGCCATCATTTTGCTCGTGGCGCACTACAT
GTACTTGATCCCAGGGCTGCAGGCAGCAGCTGCGCGTGCTGCCCAGAAGAGAAC
GGCAGCTGGCATCATGAAGAACCCTGTTGTGGATGGAATAGTGGTGACTGACATT
GACACAATGACAATTGACCCCCAAGTGGAGAAAAAGATGGGACAGGTGCTACTC
ATAGCAGTAGCCGTCTCCAGCGCCATACTGTCGCGGACCGCCTGGGGGTGGGGG
GAGGCTGGGGCCCTGATCACAGCCGCAACTTCCACTTTGTGGGAAGGCTCTCCGA
ACAAGTACTGGAACTCCTCTACAGCCACTTCACTGTGTAACATTTTTAGGGGAAG
TTACTTGGCTGGAGCTTCTCTAATCTACACAGTAACAAGAAACGCTGGCTTGGTC
AAGAGACGTGGGGGTGGAACAGGAGAGACCCTGGGAGAGAAATGGAAGGCCCG
CTTGAACCAGATGTCGGCCCTGGAGTTCTACTCCTACAAAAAGTCAGGCATCACC
GAGGTGTGCAGAGAAGAGGCCCGCCGCGCCCTCAAGGACGGTGTGGCAACGGGA
GGCCATGCTGTGTCCCGAGGAAGTGCAAAGCTGAGATGGTTGGTGGAGCGGGGA
TACCTGCAGCCCTATGGAAAGGTCATTGATCTTGGATGTGGCAGAGGGGCTGGA
GTTACTACGCCGCCACCATCCGCAAAGTTCAAGAAGTGAAAGGATACACAAAAG
GAGGCCCTGGTCATGAAGAACCCGTGTTGGTGCAAAGCTATGGGTGGAACATAG
TCCGTCTTAAGAGTGGGGTGGACGTCTTTCATATGGCGGCTGAGCCGTGTGACAC
GCTGCTGTGTGACATAGGTGAGTCATCATCTAGTCCTGAAGTGGAAGAAGCACGG
ACGCTCAGAGTCCTCTCCATGGTGGGGATTGGCTTGAAAAAAGACCAGGAGCCT
TTTGTATAAAAGTGTTGTGCCCATACACCAGCACTATGATGGAAACCCTGGAGCG
ACTGCAGCGTAGGTATGGGGGAGGACTGGTCAGAGTGCCACTCTCCCGCAACTCT
ACACATGAGATGTACTGGGTCTCTGGAGCGAAAAGCAACACCATAAAAAGTGTG
TCCACCACGAGCCAGCTCCTCTTGGGGCGCATGGACGGGCCTAGGAGGCCAGTG
AAATATGAGGAGGATGTGAATCTCGGCTCTGGCACGCGGGCTGTGGTAAGCTGC
GCTGAAGCTCCCAACATGAAGATCATTGGTAACCGCATTGAAAGGATCCGCAGTG
AGCACGCGGAAACGTGGTTCTTTGACGAGAACCACCCATATAGGACATGGGCTTA
CCATGGAAGCTATGAGGCCCCCACACAAGGGTCAGCGTCCTCTCTAATAAACGGG
GTTGTCAGGCTCCTGTCAAAACCCTGGGATGTGGTGACTGGAGTCACAGGAATAG
CCATGACCGACACCACACCGTATGGTCAGCAAAGAGTTTTCAAGGAAAAAGTGG
ACACTAGGGTGCCAGACCCCCAAGAAGGCACTCGTCAGGTTATGAGCATGGTCTC
TTCCTGGTTGTGGAAAGAGCTAGGCAAACACAAACGGCCACGAGTCTGTACCAA
```

-continued

```
AGAAGAGTTCATCAACAAGGTTCGTAGCAATGCAGCATTAGGGGCAATATTTGA

AGAGGAAAAAGAGTGGAAGACTGCAGTGGAAGCTGTGAACGATCCAAGGTTCTG

GGCTCTAGTGGACAAGGAAAGAGAGCACCACCTGAGAGGAGAGTGCCAGAGTTG

TGTGTATAACATGATGGGAAAAAGAGAAAAGAAACAAGGGGAATTTGGAAAGG

CCAAGGGCAGCCGCGCCATCTGGTATATGTGGCTAGGGGCTAGATTTCTAGAGTT

CGAAGCCCTTGGATTCTTGAACGAGGATCACTGGATGGGGAGAGAGAACTCAGG

AGGTGGTGTTGAAGGGCTGGGATTACAAAGACTCGGATATGTCCTAGAAGAGAT

GAGTCGTATACCAGGAGGAAGGATGTATGCAGATGACACTGCTGGCTGGGACAC

CCGCATTAGCAGGTTTGATCTGGAGAATGAAGCTCTAATCACCAACCAAATGGAG

AAAGGGCACAGGGCCTTGGCATTGGCCATAATCAAGTACACATACCAAAACAAA

GTGGTAAAGGTCCTTAGACCAGCTGAAAAAGGGAAAACAGTTATGGACATTATTT

CGAGACAAGACCAAAGGGGGAGCGGACAAGTTGTCACTTACGCTCTTAACACAT

TTACCAACCTAGTGGTGCAACTCATTCGGAATATGGAGGCTGAGGAAGTTCTAGA

GATGCAAGACTTGTGGCTGCTGCGGAGGTCAGAGAAAGTGACCAACTGGTTGCA

GAGCAACGGATGGGATAGGCTCAAACGAATGGCAGTCAGTGGAGATGATTGCGT

TGTGAAGCCAATTGATGATAGGTTTGCACATGCCCTCAGGTTCTTGAATGATATG

GGAAAAGTTAGAAAGGACACACAAGAGTGGAAACCCTCAACTGGATGGGACAAC

TGGGAAGAAGTTCCGTTTTGCTCCCACCACTTCAACAAGCTCCATCTCAAGGACG

GGAGGTCCATTGTGGTTCCCTGCCGCCACCAAGATGAACTGATTGGCCGGGCCCG

CGTCTCTCCAGGGGCGGGATGGAGCATCCGGGAGACTGCTTGCCTAGCAAAATCA

TATGCGCAGATGTGGCAGCTCCTTTATTTCCACAGAAGGGACCTCCGACTGATGG

CCAATGCCATTTGTTCATCTGTGCCAGTTGACTGGGTTCCAACTGGGAGAACTAC

CTGGTCAATCCATGGAAAGGGAGAATGGATGACCACTGAAGACATGCTTGTGGT

GTGGAACAGAGTGTGGATTGAGGAGAACGACCACATGGAAGACAAGACCCCAGT

TACGAAATGGACAGACATTCCCTATTTGGGAAAAAGGGAAGACTTGTGGTGTGG

ATCTCTCATAGGGCACAGACCGCGCACCACCTGGGCTGAGAACATTAAAAACAC

AGTCAACATGGTGCGCAGGATCATAGGTGATGAAGAAAAGTACATGGACTACCT

ATCCACCCAAGTTCGCTACTTGGGTGAAGAAGGGTCTACACCTGGAGTGCTGTAA

GCACCAATCTTAATGTTGTCAGGCCTGCTAGTCAGCCACAGCTTGGGGAAAGCTG

TGCAGCCTGTGACCCCCCAGGAGAAGCTGGGAAACCAAGCCTATAGTCAGGCCG

AGAACGCCATGGCACGGAAGAAGCCATGCTGCCTGTGAGCCCCTCAGAGGATAC

TGAGTCAAAAAACCCCACGCGCTTGGAGGCGCAGGATGGGAAAAGAAGGTGGCG

ACCTTCCCCACCCTTCAATCTGGGGCCTGAACTGGAGATCAGCTGTGGATCCCCA

GAAGAGGGACTAGTGGTTAGAGGAGACCCCCCGGAAAACGCAAAACAGCATATT

GACGCTGGGAAAGACCAGAGACTCCATGAGTTTCC

SEQ ID NO: 2: Genomic sequence of chimeric ZIKVBR15-MC
mutant miR4279 (10,807 nt)
AGTTGTTGATCTGTGTGAGTCAGACTGCGACAGTTCGAGTCTGAAGCGAGAGCTAACA

ACAGTATCAACAGGTTTAATTTGGATTTGGAAACGAGAGTTTCTGGTCATGAAAAACCCAAA

AAAGAAATCCGGAGGATTCCGGATTGTCAATATGCTAAAACGCGGAGTAGCCCGTGTGAGCC

CCTTTGGGGGCTTGAAGAGGCTGCCAGCCGGACTTCTGCTGGGTCATGGGCCCATCAGGATG

GTCTTGGCGATTCTAGCCTTTTTGAGATTCACGGCAATCAAGCCATCACTGGGTCTCATCAA
```

-continued

```
TAGATGGGGTTCAGTTGGGAAAAAAGAGGCTATGGAAATAATAAAGAAGTTCAAGAAAGATC

TGGCTGCCATGCTGAGAATAATCAATGCTAGGAAGGAGAAGAAGAGACGAGGCGCAGATACT

AGTGTCGGAATTGTTGGCCTCCTGCTGACCACAGCTATGGCAGCGGAGGTCACTAGACGTGG

GAGTGCATACTATATGTACTTGGACAGAAACGATGCTGGGGAGGCCATATCTTTTCCAACCA

CATTGGGGATGAATAAGTGTTATATACAGATCATGGATCTTGGACACATGTGTGATGCCACC

ATGAGCTATGAATGCCCTATGCTGGATGAGGGGGTGGAACCAGATGACGTCGATTGTTGGTG

CAACACGACGTCAACTTGGGTTGTGTACGGAACCTGCCATCACAAAAAAGGTGAAGCACGGA

GATCTAGAAGAGCTGTGACGCTCCCCTCCCATTCCACTAGGAAGCTGCAAACGCGGTCGCAA

ACCTGGTTGGAATCAAGAGAATACACAAAGCACTTGATTAGAGTCGAAAATTGGATATTCAG

GAACCCTGGCTTCGCGTTAGCAGCAGCTGCCATCGCTTGGCTTTTGGGAAGCTCAACGAGCC

AAAAAGTCATATACTTGGTCATGATACTGCTGATTGCCCCGGCATACAGCATCAGGTGCATA

GGAGTCAGCAATAGGGACTTTGTGGAAGGTATGTCAGGTGGGACTTGGGTTGATGTTGTCTT

GGAACATGGAGGTTGTGTCACCGTAATGGCACAGGACAAACCGACTGTCGACATAGAGCTGG

TTACAACAACAGTCAGCAACATGGCGGAGGTACGATCGTACTGCTATGAGGCATCAATATCA

GACATGGCTTCGGACAGCCGCTGCCCAACACAAGGTGAAGCCTACCTTGACAAGCAATCAGA

CACTCAATATGTCTGCAAAAGAACGTTAGTGGACAGAGGCTGGGGAAATGGATGTGGACTTT

TTGGCAAAGGGAGCCTGGTGACATGCGCTAAGTTTGCATGCTCCAAGAAAATGACCGGGAAG

AGCATCCAGCCAGAGAATCTGGAGTACCGGATAATGCTGTCAGTTCATGGCTCCCAGCACAG

TGGGATGATCGTTAATGACACAGGACATGAAACTGATGAGAATAGAGCGAAAGTTGAGATAA

CGCCCAATTCACCAAGAGCCGAAGCCACCCTGGGGGGTTTTGGAAGCCTAGGACTTGATTGT

GAACCGAGGACAGGCCTTGACTTTTCAGATTTGTATTACTTGACTATGAATAACAAGCACTG

GTTGGTTCACAAGGAGTGGTTCCACGACATTCCATTACCTTGGCACGCTGGGGCAGACACCG

GAACTCCACACTGGAACAACAAAGAAGCACTGGTAGAGTTCAAGGACGCACATGCCAAAAGG

CAAACTGTCGTGGTTCTAGGGAGTCAAGAAGGAGCAGTTCACACGGCCCTTGCTGGAGCTCT

GGAGGCTGAGATGGATGGTGCAAAGGGAAGGCTGTCCTCTGGCCACTTGAAATGTCGCCTGA

AAATGGATAAACTTAGATTGAAGGGCGTGTCATACTCCTTGTGTACTGCAGCGTTCACATTC

ACCAAGATCCCGGCTGAAACACTGCACGGGACAGTCACAGTGGAGGTACAGTACGCAGGGAC

AGATGGACCTTGCAAGGTTCCAGCTCAGATGGCGGTGGACATGCAAACTCTGACCCCAGTTG

GGAGGTTGATAACCGCTAACCCCGTAATCACTGAAAGCACTGAGAACTCTAAGATGATGCTG

GAACTTGATCCACCATTTGGGGACTCTTACATTGTCATAGGAGTCGGGGAGAAGAAGATCAC

CCACCACTGGCACAGGAGTGGCAGCACCATTGGAAAAGCATTTGAGGCCACTGTGAGAGGCG

CCAAGAGAATGGCAGTCCTGGGGGACACAGCCTGGGACTTTGGATCAGTTGGAGGCGCTCTC

AACTCATTGGGCAAGGGCATCCATCAAATTTTTGGAGCAGCTTTCAAATCATTGTTTGGAGG

AATGTCCTGGTTCTCACAAATTCTCATTGGAACGTTGCTGATGTGGTTGGGTCTGAACACAA

AGAATGGATCTATTTCCCTTATGTGCTTGGCCTTAGGGGGGGTGTTGATCTTCTTATCCACA

GCCGTCTCTGCTGATGTGGGGTGCTCGGTGGACTTCTCAAAGAAGGAGACGAGATGCGGTAC

AGGGGTGTTCGTCTATAACGACGTTGAAGCCTGGAGGGACAGGTACAAGTACCATCCTGACT

CCCCCCGTAGATTGGCAGCAGCAGTCAAGCAAGCCTGGGAAGATGGTATCTGCGGGATCTCC

TCTGTTTCAAGAATGGAAAACATCATGTGGAGATCAGTAGAAGGGGAGCTCAACG**CtATCCT
aGAgGAGAA**TGGAGTTCAACTGACGGTCGTTGTGGGATCTGTAAAAAACCCCATGTGGAGAG

GTCCACAGAGATTGCCCGTGCCTGTGAACGAGCTGCCCCACGGCTGGAAGGCTTGGGGGAAA
```

-continued

```
TCGTACTTCGTCAGAGCAGCAAAGACAAATAACAGCTTTGTCGTGGATGGTGACACACTGAA

GGAATGCCCACTCAAACATAGAGCATGGAACAGCTTTCTTGTGGAGGATCATGGGTTCGGGG

TATTTCACACTAGTGTCTGGCTCAAGGTTAGAGAAGATTATTCATTAGAGTGTGATCCAGCC

GTTATTGGAACAGCTGTTAAGGGAAAGGAGGCTGTACACAGTGATCTAGGCTACTGGATTGA

GAGTGAGAAGAATGACACATGGAGGCTGAAGAGGGCCCATCTGATCGAGATGAAAACATGTG

AATGGCCAAAGTCCCACACATTGTGGACAGATGGAATAGAAGAGAGTGATCTGATCATACCC

AAGTCTTTAGCTGGGCCACTCAGCCATCACAATACCAGAGAGGGCTACAGGACCCAAATGAA

AGGGCCATGGCACAGTGAAGAGCTTGAAATTCGGTTTGAGGAATGCCCAGGCACTAAGGTtt

ACGTGGAGGAgACATGTGGAACAAGAGGACCATCTCTGAGATCAACCACTGCAAGCGGAAGG

GTGATCGAGGAATGGTGCTGCAGGGAGTGCACAATGCCCCCACTGTCGTTCCGGGCTAAAGA

TGGCTGTTGGTATGGAATGGAGATAAGGCCCAGGAAAGAACCAGAAAGCAACTTAGTAAGGT

CAATGGTGACTGCAGGATCAACTGATCACATGGACCACTTCTCCCTTGGAGTGCTTGTGATC

CTGCTCATGGTGCAGGAAGGGCTGAAGAAGAGAATGACCACAAAGATCATCATAAGCACATC

AATGGCAGTGCTGGTAGCTATGATCCTGGGAGGATTTTCAATGAGTGACCTGGCTAAGCTTG

CAATTTTGATGGGTGCCACCTTCGCGGAAATGAACACTGGAGGAGATGTAGCTCATCTGGCG

CTGATAGCGGCATTCAAAGTCAGACCAGCGTTGCTGGTATCTTTCATCTTCAGAGCTAATTG

GACACCCCGTGAAAGCATGCTGCTGGCCTTGGCCTCGTGTCTTTTGCAAACTGCGATCTCCG

CCTTGGAAGGCGACCTGATGGTTCTCATCAATGGTTTTGCTTTGGCCTGGTTGGCAATACGA

GCGATGGTTGTTCCACGCACTGATAACATCACCTTGGCAATCCTGGCTGCTCTGACACCACT

GGCCCGGGGCACACTGCTTGTGGCGTGGAGAGCAGGCCTTGCTACTTGCGGGGGGTTTATGC

TCCTCTCTCTGAAGGGAAAAGGCAGTGTGAAGAAGAACTTACCATTTGTCATGGCCCTGGGA

CTAACCGCTGTGAGGCTGGTCGACCCCATCAACGTGGTGGGACTGCTGTTACTCACAAGGAG

TGGGAAGCGGAGCTGGCCCCCTAGCGAAGTACTCACAGCTGTTGGCCTGATATGCGCATTGG

CTGGAGGGTTCGCCAAGGCAGATATAGAGATGGCTGGGCCCATGGCCGCGGTCGGTCTGCTA

ATTGTCAGTTACGTGGTCTCAGGAAAGAGTGTGGACATGTACATTGAAAGAGCAGGTGACAT

CACATGGGAAAAAGATGCGGAAGTCACTGGAAACAGTCCCCGGCTCGATGTGGCGCTAGATG

AGAGTGGTGATTTCTCCCTGGTGGAGGATGACGGTCCCCCCATGAGAGAGATCATACTCAAG

GTGGTCCTGATGACCATCTGTGGCATGAATCCAATAGCCATACCCTTTGCAGCTGGAGCGTG

GTACGTATACGTGAAGACTGGAAAAAGGAGTGGTGCTCTATGGGATGTGCCTGCTCCCAAGG

AAGTAAAAAAGGGGGAGACCACAGATGGAGTGTACAGAGTAATGACTCGTAGACTGCTAGGT

TCAACACAAGTTGGAGTGGGAGTTATGCAAGAGGGGGTCTTTCACACTATGTGGCACGTCAC

AAAAGGATCCGCGCTGAGAAGCGGTGAAGGGAGACTTGATCCATACTGGGGAGATGTCAAGC

AGGATCTGGTGTCATACTGTGGTCCATGGAAGCTAGATGCCGCCTGGGACGGGCACAGCGAG

GTGCAGCTCTTGGCCGTGCCCCCCGGAGAGAGAGCGAGGAACATCCAGACTCTGCCCGGAAT

ATTTAAGACAAAGGATGGGGACATTGGAGCGGTTGCGCTGGATTACCCAGCAGGAACTTCAG

GATCTCCAATCCTAGACAAGTGTGGGAGAGTGATAGGACTTTATGGCAATGGGTCGTGATC

AAAAATGGGAGTTATGTTAGTGCCATCACCCAAGGGAaGAGGGAgGAgGAGACTCCTGTTGA

GTGCTTCGAGCCCTCGATGCTGAAGAAGAAGCAGCTAACTGTCTTAGACTTGCATCCTGGAG

CTGGGAAAACCAGGAGAGTTCTTCCTGAAATAGTCCGTGAAGCCATAAAAACAAGACTCCGT

ACTGTGATCTTAGCTCCAACCAGGGTTGTCGCTGCTGAAATGGAGGAGGCCCTTAGAGGGCT

TCCAGTGCGTTATATGACAACAGCAGTCAATGTCACCCACTCTGGAACAGAAATCGTCGACT
```

-continued

TAATGTGCCATGCCACCTTCACTTCACGTCTACTACAGCCAATCAGAGTCCCCAACTATAAT

CTGTATATTATGGATGAGGCCCACTTCACAGATCCCTCAAGTATAGCAGCAAGAGGATACAT

TTCAACAAGGGTTGAGATGGGCGAGGCGGCTGCCATCTTCATGACCGCCACGCCACCAGGAA

CCCGTGACGCATTTCCGGACTCCAACTCACCAATTATGGACACCGAAGTGGAAGTCCCAGAG

AGAGCCTGGAGCTCAGGCTTTGATTGGGTGACGGATCATTCTGGAAAAACAGTTTGGTTTGT

TCCAAGCGTGAGGAACGGCAATGAGATCGCAGCTTGTCTGACAAAGGCTGGAAAACGGGTCA

TACAGCTCAGCAGAAAGACTTTTGAGACAGAGTTCCAGAAAACAAAACATCAAGAGTGGGAC

TTTGTCGTGACAACTGACATTTCAGAGATGGGCGCCAACTTTAAAGCTGACCGTGTCATAGA

TTCCAGGAGATGCCTAAAGCCGGTCATACTTGATGGCGAGAGAGTCATTCTGGCTGGACCCA

TGCCTGTCACACATGCCAGCGCTGCtCAGAGGAGaGGGCGCATAGGCAGGAATCCCAACAAA

CCTGGAGATGAGTATCTGTATGGAGGTGGGTGCGCAGAGACTGACGAAGACCATGCACACTG

GCTTGAAGCAAGAATGCTCCTTGACAATATTTACCTCCAAGATGGCCTCATAGCCTCGCTCT

ATCGACCTGAGGCCGACAAAGTAGCAGCCATTGAGGGAGAGTTCAAGCTTAGGACGGAGCAA

AGGAAGACCTTTGTGGAACTCATGAAgAGAGGAGAcCTTCCTGTTTGGCTGGCCTATCAGGT

TGCATCTGCCGGAATAACCTACACAGATAGAAGATGGTGCTTTGATGGCACGACCAACAACA

CCATAATGGAAGATAGTGTGCCGGCAGAGGTGTGGACCAGACACGGAGAGAAAAGAGTGCTC

AAACCGAGGTGGATGGACGCCAGAGTTTGTTCAGATCATGCGGCCCTGAAGTCATTCAAGGA

GTTTGCCGCTGGGAAAAGAGGAGCGGCTTTTGGAGTGATGGAAGCCCTGGGAACACTGCCAG

GACACATGACAGAGAGATTCCAGGAAGCCATTGACAACCTCGCTGTGCTCATGCGGGCAGAG

ACTGGAAGCAGGCCTTACAAAGCCGCGGCGGCCCAATTGCCGGAGACCCTAGAGACCATAAT

GCTTTTGGGGTTGCTGGGAACAGTCTCGCTGGGAATCTTCTTCGTCTTGATGAGGAACAAGG

GCATAGGGAAGATGGGCTTTGGAATGGTGACTCTTGGGGCCAGCGCATGGCTCATGTGGCTC

TCGGAAATTGAGCCAGCCAGAATTGCATGTGTCCTCATTGTTGTGTTCCTATTGCTGGTGGT

GCTCATACCTGAGCCAGAAAAGCAAAGATCTCCCCAGGACAACCAAATGGCAATCATCATCA

TGGTAGCAGTAGGTCTTCTGGGCTTGATTACCGCCAATGAACTCGGATGGTTGGAGAGAACA

AAGAGTGACCTAAGCCATCTAATGGGAAGGAGAGAGGAGGGGCAACCATAGGATTCTCAAT

GGACATTGACCTGCGGCCAGCCTCAGCTTGGGCCATCTATGCTGCCTTGACAACTTTCATTA

CCCCAGCCGTCCAACATGCAGTGACCACTTCATACAACAACTACTCCTTAATGGCGATGGCC

ACGCAAGCTGGAGTGTTGTTTGGTATGGGCAAAGGGATGCCATTCTACGCATGGGACTTTGG

AGTCCCGCTGCTAATGATAGGTTGCTACTCACAATTAACACCCCTGACCCTAATAGTGGCCA

TCATTTTGCTCGTGGCGCACTACATGTACTTGATCCCAGGGCTGCAGGCAGCAGCTGCGCGT

GCTGCCCAGAAGAGAACGGCAGCTGGCATCATGAAGAACCCTGTTGTGGATGGAATAGTGGT

GACTGACATTGACACAATGACAATTGACCCCCAAGTGGAGAAAAAGATGGGACAGGTGCTAC

TCATAGCAGTAGCCGTCTCCAGCGCCATACTGTCGCGGACCGCCTGGGGGTGGGGGGAGGCT

GGGGCCCTGATCACAGCCGCAACTTCCACTTTGTGGGAAGGCTCTCCGAACAAGTACTGGAA

CTCCTCTACAGCCACTTCACTGTGTAACATTTTTAGGGGAAGTTACTTGGCTGGAGCTTCTC

TAATCTACACAGTAACAAGAAACGCTGGCTTGGTCAAGAGACGTGGGGGTGGAACAGGAGAG

ACCCTGGGAGAGAAATGGAAGGCCCGCTTGAACCAGATGTCGGCCCTGGAGTTCTACTCCTA

CAAAAAGTCAGGCATCACCGAGGTGTGCAGAGAAGAGGCCCGCCGCGCCCTCAAGGACGGTG

TGGCAACGGGAGGCCATGCTGTGTCCCGAGGAAGTGCAAAGCTGAGATGGTTGGTGGAGCGG

GGATACCTGCAGCCCTATGGAAAGGTCATTGATCTTGGATGTGGCAGAGGGGGCTGGAGTTA

-continued

```
CTACGCCGCCACCATCCGCAAAGTTCAAGAAGTGAAAGGATACACAAAAGGAGGCCCTGGTC
ATGAAGAACCCGTGTTGGTGCAAAGCTATGGGTGGAACATAGTCCGTCTTAAGAGTGGGGTG
GACGTCTTTCATATGGCGGCTGAGCCGTGTGACACGCTGCTGTGTGACATAGGTGAGTCATC
ATCTAGTCCTGAAGTGGAAGAAGCACGGACGCTCAGAGTCCTCTCCATGGTGGGGGATTGGC
TTGAAAAAGACCAGGAGCCTTTTGTATAAAAGTGTTGTGCCCATACACCAGCACTATGATG
GAAACCCTGGAGCGACTGCAGCGTAGGTATGGGGAGGACTGGTCAGAGTGCCACTCTCCCG
CAACTCTACACATGAGATGTACTGGGTCTCTGGAGCGAAAAGCAACACCATAAAAGTGTGT
CCACCACGAGCCAGCTCCTCTTGGGGCGCATGGACGGGCCTAGGAGGCCAGTGAAATATGAG
GAGGATGTGAATCTCGGCTCTGGCACGCGGGCTGTGGTAAGCTGCGCTGAAGCTCCCAACAT
GAAGATCATTGGTAACCGCATTGAAAGGATCCGCAGTGAGCACGCGGAAACGTGGTTCTTTG
ACGAGAACCACCCATATAGGACATGGGCTTACCATGGAAGCTATGAGGCCCCCACACAAGGG
TCAGCGTCCTCTCTAATAAACGGGGTTGTCAGGCTCCTGTCAAAACCCTGGGATGTGGTGAC
TGGAGTCACAGGAATAGCCATGACCGACACCACACCGTATGGTCAGCAAAGAGTTTTCAAGG
AAAAAGTGGACACTAGGGTGCCAGACCCCCAAGAAGGCACTCGTCAGGTTATGAGCATGGTC
TCTTCCTGGTTGTGGAAAGAGCTAGGCAAACACAAACGGCCACGAGTCTGTACCAAAGAAGA
GTTCATCAACAAGGTTCGTAGCAATGCAGCATTAGGGGCAATATTTGAAGAGGAAAAGAGT
GGAAGACTGCAGTGGAAGCTGTGAACGATCCAAGGTTCTGGGCTCTAGTGGACAAGGAAAGA
GAGCACCACCTGAGAGGAGAGTGCCAGAGTTGTGTGTATAACATGATGGGAAAAAGAGAAAA
GAAACAAGGGGAATTTGGAAAGGCCAAGGGCAGCCGCGCCATCTGGTATATGTGGCTAGGGG
CTAGATTTCTAGAGTTCGAAGCCCTTGGATTCTTGAACGAGGATCACTGGATGGGGAGAGAG
AACTCAGGAGGTGGTGTTGAAGGGCTGGGATTACAAAGACTCGGATATGTCCTAGAAGAGAT
GAGTCGTATACCAGGAGGAAGGATGTATGCAGATGACACTGCTGGCTGGGACACCCGCATTA
GCAGGTTTGATCTGGAGAATGAAGCTCTAATCACCAACCAAATGGAGAAAGGGCACAGGGCC
TTGGCATTGGCCATAATCAAGTACACATACCAAAACAAAGTGGTAAAGGTCCTTAGACCAGC
TGAAAAAGGGAAAACAGTTATGGACATTATTTCGAGACAAGACCAAAGGGGGAGCGGACAAG
TTGTCACTTACGCTCTTAACACATTTACCAACCTAGTGGTGCAACTCATTCGGAATATGGAG
GCTGAGGAAGTTCTAGAGATGCAAGACTTGTGGCTGCTGCGGAGGTCAGAGAAAGTGACCAA
CTGGTTGCAGAGCAACGGATGGGATAGGCTCAAACGAATGGCAGTCAGTGGAGATGATTGCG
TTGTGAAGCCAATTGATGATAGGTTTGCACATGCCCTCAGGTTCTTGAATGATATGGGAAAA
GTTAGAAAGGACACACAAGAGTGGAAACCCTCAACTGGATGGGACAACTGGGAAGAAGTTCC
GTTTTGCTCCCACCACTTCAACAAGCTCCATCTCAAGGACGGGAGGTCCATTGTGGTTCCCT
GCCGCCACCAAGATGAACTGATTGGCCGGGCCCGCGTCTCTCCAGGGGCGGGATGGAGCATC
CGGGAGACTGCTTGCCTAGCAAAATCATATGCGCAGATGTGGCAGCTCCTTTATTTCCACAG
AAGGGACCTCCGACTGATGGCCAATGCCATTTGTTCATCTGTGCCAGTTGACTGGGTTCCAA
CTGGGAGAACTACCTGGTCAATCCATGGAAAGGGAGAATGGATGACCACTGAAGACATGCTT
GTGGTGTGGAACAGAGTGTGGATTGAGGAGAACGACCACATGGAAGACAAGACCCCAGTTAC
GAAATGGACAGACATTCCCTATTTGGGAAAAAGGGAAGACTTGTGGTGTGGATCTCTCATAG
GGCACAGACCGCGCACCACCTGGGCTGAGAACATTAAAAACACAGTCAACATGGTGCGCAGG
ATCATAGGTGATGAAGAAAAGTACATGGACTACCTATCCACCCAAGTTCGCTACTTGGGTGA
AGAAGGGTCTACACCTGGAGTGCTGTAAGCACCAATTTTAGTGTTGTCAGGCCTGCTAGTCA
GCCACAGTTTGGGGAAAGCTGTGCAGCCTGTAACCCCCCCAGGAGAAGCTGGGAAACCAAGC
```

-continued

```
TCATAGTCAGGCCGAGAACGCCATGGCACGGAAGAAGCCATGCTGCCTGTGAGCCCCTCAGA
GGACACTGAGTCAAAAAACCCCACGCGCTTGGAAGCGCAGGATGGGAAAAGAAGGTGGCGAC
CTTCCCCACCCTTCAATCTGGGGCCTGAACTGGAGACTAGCTGTGAATCTCCAGCAGAGGGA
CTAGTGGTTAGAGGAGACCCCCCGGAAAACGCAAAACAGCATATTGACGCTGGGAAAGACCA
GAGACTCCATGAGTTTCCACCACGCTGGCCGCCAGGCACAGATCGCCGAACAGCGGCGGCCG
GTGTGGGGAAATCCATGGTTTCT
```

SEQ ID NO: 3: Genomic sequence of chimeric ZIKVBR15-MC mutant miR4279 (10,807 nt) Bold and underlined-miR targeted sequences; bold and italic glycosylation site

```
AGTTGTTGATCTGTGTGAGTCAGACTGCGACAGTTCGAGTCTGAAGCGAGAGCTAACA
ACAGTATCAACAGGTTTAATTTGGATTTGGAAACGAGAGTTTCTGGTCATGAAAAACCCAAA
AAAGAAATCCGGAGGATTCCGGATTGTCAATATGCTAAAACGCGGAGTAGCCCGTGTGAGCC
CCTTTGGGGGCTTGAAGAGGCTGCCAGCCGGACTTCTGCTGGGTCATGGGCCCATCAGGATG
GTCTTGGCGATTCTAGCCTTTTTGAGATTCACGGCAATCAAGCCATCACTGGGTCTCATCAA
TAGATGGGGTTCAGTTGGGAAAAAAGAGGCTATGGAAATAATAAAGAAGTTCAAGAAAGATC
TGGCTGCCATGCTGAGAATAATCAATGCTAGGAAGGAGAAGAAGAGACGAGGCGCAGATACT
AGTGTCGGAATTGTTGGCCTCCTGCTGACCACAGCTATGGCAGCGGAGGTCACTAGACGTGG
GAGTGCATACTATATGTACTTGGACAGAAACGATGCTGGGGAGGCCATATCTTTTCCAACCA
CATTGGGGATGAATAAGTGTTATATACAGATCATGGATCTTGGACACATGTGTGATGCCACC
ATGAGCTATGAATGCCCTATGCTGGATGAGGGGGTGGAACCAGATGACGTCGATTGTTGGTG
CAACACGACGTCAACTTGGGTTGTGTACGGAACCTGCCATCACAAAAAAGGTGAAGCACGGA
GATCTAGAAGAGCTGTGACGCTCCCCTCCCATTCCACTAGGAAGCTGCAAACGCGGTCGCAA
ACCTGGTTGGAATCAAGAGAATACACAAAGCACTTGATTAGAGTCGAAAATTGGATATTCAG
GAACCCTGGCTTCGCGTTAGCAGCAGCTGCCATCGCTTGGCTTTTGGGAAGCTCAACGAGCC
AAAAAGTCATATACTTGGTCATGATACTGCTGATTGCCCCGGCATACAGCATCAGGTGCATA
GGAGTCAGCAATAGGGACTTTGTGGAAGGTATGTCAGGTGGGACTTGGGTTGATGTTGTCTT
GGAACATGGAGGTTGTGTCACCGTAATGGCACAGGACAAACCGACTGTCGACATAGAGCTGG
TTACAACAACAGTCAGCAACATGGCGGAGGTACGATCGTACTGCTATGAGGCATCAATATCA
GACATGGCTTCGGACAGCCGCTGCCCAACACAAGGTGAAGCCTACCTTGACAAGCAATCAGA
CACTCAATATGTCTGCAAAAGAACGTTAGTGGACAGAGGCTGGGGAAATGGATGTGGACTTT
TTGGCAAAGGGAGCCTGGTGACATGCGCTAAGTTTGCATGCTCCAAGAAAATGACCGGGAAG
AGCATCCAGCCAGAGAATCTGGAGTACCGGATAATGCTGTCAGTTCATGGCTCCCAGCACAG
TGGGAT**G*ActGTcAATGAtAtAGGAtAT***GAAACTGATGAGAATAGAGCGAAAGTTGAGATAA
CGCCCAATTCACCAAGAGCCGAAGCCACCCTGGGGGGTTTTGGAAGCCTAGGACTTGATTGT
GAACCGAGGACAGGCCTTGACTTTTCAGATTTGTATTACTTGACTATGAATAACAAGCACTG
GTTGGTTCACAAGGAGTGGTTCCACGACATTCCATTACCTTGGCACGCTGGGGCAGACACCG
GAACTCCACACTGGAACAACAAAGAAGCACTGGTAGAGTTCAAGGACGCACATGCCAAAAGG
CAAACTGTCGTGGTTCTAGGGAGTCAAGAAGGAGCAGTTCACACGGCCCTTGCTGGAGCTCT
GGAGGCTGAGATGGATGGTGCAAAGGGAAGGCTGTCCTCTGGCCACTTGAAATGTCGCCTGA
AAATGGATAAACTTAGATTGAAGGGCGTGTCATACTCCTTGTGTACTGCAGCGTTCACATTC
ACCAAGATCCCGGCTGAAACACTGCACGGGACAGTCACAGTGGAGGTACAGTACGCAGGGAC
AGATGGACCTTGCAAGGTTCCAGCTCAGATGGCGGTGGACATGCAAACTCTGACCCCAGTTG
```

-continued

GGAGGTTGATAACCGCTAACCCCGTAATCACTGAAAGCACTGAGAACTCTAAGATGATGCTG

GAACTTGATCCACCATTTGGGGACTCTTACATTGTCATAGGAGTCGGGGAGAAGAAGATCAC

CCACCACTGGCACAGGAGTGGCAGCACCATTGGAAAAGCATTTGAGGCCACTGTGAGAGGCG

CCAAGAGAATGGCAGTCCTGGGGGACACAGCCTGGGACTTTGGATCAGTTGGAGGCGCTCTC

AACTCATTGGGCAAGGGCATCCATCAAATTTTTGGAGCAGCTTTCAAATCATTGTTTGGAGG

AATGTCCTGGTTCTCACAAATTCTCATTGGAACGTTGCTGATGTGGTTGGGTCTGAACACAA

AGAATGGATCTATTTCCCTTATGTGCTTGGCCTTAGGGGGGTGTTGATCTTCTTATCCACA

GCCGTCTCTGCTGATGTGGGGTGCTCGGTGGACTTCTCAAAGAAGGAGACGAGATGCGGTAC

AGGGGTGTTCGTCTATAACGACGTTGAAGCCTGGAGGGACAGGTACAAGTACCATCCTGACT

CCCCCCGTAGATTGGCAGCAGCAGTCAAGCAAGCCTGGGAAGATGGTATCTGCGGGATCTCC

TCTGTTTCAAGAATGGAAAACATCATGTGGAGATCAGTAGAAGGGGAGCTCAACGctATCCT aGAgGAGAATGGAGTTCAACTGACGGTCGTTGTGGGATCTGTAAAAAACCCCATGTGGAGAG

GTCCACAGAGATTGCCCGTGCCTGTGAACGAGCTGCCCCACGGCTGGAAGGCTTGGGGGAAA

TCGTACTTCGTCAGAGCAGCAAAGACAAATAACAGCTTTGTCGTGGATGGTGACACACTGAA

GGAATGCCCACTCAAACATAGAGCATGGAACAGCTTTCTTGTGGAGGATCATGGGTTCGGGG

TATTTCACACTAGTGTCTGGCTCAAGGTTAGAGAAGATTATTCATTAGAGTGTGATCCAGCC

GTTATTGGAACAGCTGTTAAGGGAAAGGAGGCTGTACACAGTGATCTAGGCTACTGGATTGA

GAGTGAGAAGAATGACACATGGAGGCTGAAGAGGGCCCATCTGATCGAGATGAAAACATGTG

AATGGCCAAAGTCCCACACATTGTGGACAGATGGAATAGAAGAGAGTGATCTGATCATACCC

AAGTCTTTAGCTGGGCCACTCAGCCATCACAATACCAGAGAGGGCTACAGGACCCAAATGAA

AGGGCCATGGCACAGTGAAGAGCTTGAAATTCGGTTTGAGGAATGCCCAGGCACTAAGGTtt

ACGTGGAGGAgACATGTGGAACAAGAGGACCATCTCTGAGATCAACCACTGCAAGCGGAAGG

GTGATCGAGGAATGGTGCTGCAGGGAGTGCACAATGCCCCACTGTCGTTCCGGGCTAAAGA

TGGCTGTTGGTATGGAATGGAGATAAGGCCCAGGAAAGAACCAGAAAGCAACTTAGTAAGGT

CAATGGTGACTGCAGGATCAACTGATCACATGGACCACTTCTCCCTTGGAGTGCTTGTGATC

CTGCTCATGGTGCAGGAAGGGCTGAAGAAGAGAATGACCACAAAGATCATCATAAGCACATC

AATGGCAGTGCTGGTAGCTATGATCCTGGGAGGATTTTCAATGAGTGACCTGGCTAAGCTTG

CAATTTTGATGGGTGCCACCTTCGCGGAAATGAACACTGGAGGAGATGTAGCTCATCTGGCG

CTGATAGCGGCATTCAAAGTCAGACCAGCGTTGCTGGTATCTTTCATCTTCAGAGCTAATTG

GACACCCCGTGAAAGCATGCTGCTGGCCTTGGCCTCGTGTCTTTTGCAAACTGCGATCTCCG

CCTTGGAAGGCGACCTGATGGTTCTCATCAATGGTTTTGCTTTGGCCTGGTTGGCAATACGA

GCGATGGTTGTTCCACGCACTGATAACATCACCTTGGCAATCCTGGCTGCTCTGACACCACT

GGCCCGGGGCACACTGCTTGTGGCGTGGAGAGCAGGCCTTGCTACTTGCGGGGGGTTTATGC

TCCTCTCTCTGAAGGGAAAAGGCAGTGTGAAGAAGAACTTACCATTTGTCATGGCCCTGGGA

CTAACCGCTGTGAGGCTGGTCGACCCCATCAACGTGGTGGGACTGCTGTTACTCACAAGGAG

TGGGAAGCGGAGCTGGCCCCCTAGCGAAGTACTCACAGCTGTTGGCCTGATATGCGCATTGG

CTGGAGGGTTCGCCAAGGCAGATATAGAGATGGCTGGGCCCATGGCCGCGGTCGGTCTGCTA

ATTGTCAGTTACGTGGTCTCAGGAAAGAGTGTGGACATGTACATTGAAAGAGCAGGTGACAT

CACATGGGAAAAAGATGCGGAAGTCACTGGAAACAGTCCCCGGCTCGATGTGGCGCTAGATG

AGAGTGGTGATTTCTCCCTGGTGGAGGATGACGGTCCCCCCATGAGAGAGATCATACTCAAG

GTGGTCCTGATGACCATCTGTGGCATGAATCCAATAGCCATACCCTTTGCAGCTGGAGCGTG

```
GTACGTATACGTGAAGACTGGAAAAAGGAGTGGTGCTCTATGGGATGTGCCTGCTCCCAAGG

AAGTAAAAAAGGGGGAGACCACAGATGGAGTGTACAGAGTAATGACTCGTAGACTGCTAGGT

TCAACACAAGTTGGAGTGGGAGTTATGCAAGAGGGGGTCTTTCACACTATGTGGCACGTCAC

AAAAGGATCCGCGCTGAGAAGCGGTGAAGGGAGACTTGATCCATACTGGGGAGATGTCAAGC

AGGATCTGGTGTCATACTGTGGTCCATGGAAGCTAGATGCCGCCTGGGACGGGCACAGCGAG

GTGCAGCTCTTGGCCGTGCCCCCCGGAGAGAGAGCGAGGAACATCCAGACTCTGCCCGGAAT

ATTTAAGACAAAGGATGGGGACATTGGAGCGGTTGCGCTGGATTACCCAGCAGGAACTTCAG

GATCTCCAATCCTAGACAAGTGTGGGAGAGTGATAGGACTTTATGGCAATGGGGTCGTGATC

AAAAATGGGAGTTATGTTAGTGCCATCACCCAAGGGAaGAGGGAgGAgGAGACTCCTGTTGA

GTGCTTCGAGCCCTCGATGCTGAAGAAGAAGCAGCTAACTGTCTTAGACTTGCATCCTGGAG

CTGGGAAAACCAGGAGAGTTCTTCCTGAAATAGTCCGTGAAGCCATAAAAACAAGACTCCGT

ACTGTGATCTTAGCTCCAACCAGGGTTGTCGCTGCTGAAATGGAGGAGGCCCTTAGAGGGCT

TCCAGTGCGTTATATGACAACAGCAGTCAATGTCACCCACTCTGGAACAGAAATCGTCGACT

TAATGTGCCATGCCACCTTCACTTCACGTCTACTACAGCCAATCAGAGTCCCCAACTATAAT

CTGTATATTATGGATGAGGCCCACTTCACAGATCCCTCAAGTATAGCAGCAAGAGGATACAT

TTCAACAAGGGTTGAGATGGGCGAGGCGGCTGCCATCTTCATGACCGCCACGCCACCAGGAA

CCCGTGACGCATTTCCGGACTCCAACTCACCAATTATGGACACCGAAGTGGAAGTCCCAGAG

AGAGCCTGGAGCTCAGGCTTTGATTGGGTGACGGATCATTCTGGAAAAACAGTTTGGTTTGT

TCCAAGCGTGAGGAACGGCAATGAGATCGCAGCTTGTCTGACAAAGGCTGGAAAACGGGTCA

TACAGCTCAGCAGAAAGACTTTTGAGACAGAGTTCCAGAAAACAAAACATCAAGAGTGGGAC

TTTGTCGTGACAACTGACATTTCAGAGATGGGCGCCAACTTTAAAGCTGACCGTGTCATAGA

TTCCAGGAGATGCCTAAAGCCGGTCATACTTGATGGCGAGAGAGTCATTCTGGCTGGACCCA

TGCCTGTCACACATGCCAGCGCTGCtCAGAGGAGaGGGCGCATAGGCAGGAATCCCAACAAA

CCTGGAGATGAGTATCTGTATGGAGGTGGGTGCGCAGAGACTGACGAAGACCATGCACACTG

GCTTGAAGCAAGAATGCTCCTTGACAATATTTACCTCCAAGATGGCCTCATAGCCTCGCTCT

ATCGACCTGAGGCCGACAAAGTAGCAGCCATTGAGGGAGAGTTCAAGCTTAGGACGGAGCAA

AGGAAGACCTTTGTGGAACTCATGAAgAGAGGAGAcCTTCCTGTTTGGCTGGCCTATCAGGT

TGCATCTGCCGGAATAACCTACACAGATAGAAGATGGTGCTTTGATGGCACGACCAACAACA

CCATAATGGAAGATAGTGTGCCGGCAGAGGTGTGGACCAGACACGGAGAGAAAAGAGTGCTC

AAACCGAGGTGGATGGACGCCAGAGTTTGTTCAGATCATGCGGCCCTGAAGTCATTCAAGGA

GTTTGCCGCTGGGAAAAGAGGAGCGGCTTTTGGAGTGATGGAAGCCCTGGGAACACTGCCAG

GACACATGACAGAGAGATTCCAGGAAGCCATTGACAACCTCGCTGTGCTCATGCGGGCAGAG

ACTGGAAGCAGGCCTTACAAAGCCGCGGCGGCCCAATTGCCGGAGACCCTAGAGACCATAAT

GCTTTTGGGGTTGCTGGGAACAGTCTCGCTGGGAATCTTCTTCGTCTTGATGAGGAACAAGG

GCATAGGGAAGATGGGCTTTGGAATGGTGACTCTTGGGGCCAGCGCATGGCTCATGTGGCTC

TCGGAAATTGAGCCAGCCAGAATTGCATGTGTCCTCATTGTTGTGTTCCTATTGCTGGTGGT

GCTCATACCTGAGCCAGAAAAGCAAAGATCTCCCCAGGACAACCAAATGGCAATCATCATCA

TGGTAGCAGTAGGTCTTCTGGGCTTGATTACCGCCAATGAACTCGGATGGTTGGAGAGAACA

AAGAGTGACCTAAGCCATCTAATGGGAAGGAGAGAGGAGGGGGCAACCATAGGATTCTCAAT

GGACATTGACCTGCGGCCAGCCTCAGCTTGGGCCATCTATGCTGCCTTGACAACTTTCATTA

CCCCAGCCGTCCAACATGCAGTGACCACTTCATACAACAACTACTCCTTAATGGCGATGGCC
```

-continued

```
ACGCAAGCTGGAGTGTTGTTTGGTATGGGCAAAGGGATGCCATTCTACGCATGGGACTTTGG
AGTCCCGCTGCTAATGATAGGTTGCTACTCACAATTAACACCCCTGACCCTAATAGTGGCCA
TCATTTTGCTCGTGGCGCACTACATGTACTTGATCCCAGGGCTGCAGGCAGCAGCTGCGCGT
GCTGCCCAGAAGAGAACGGCAGCTGGCATCATGAAGAACCCTGTTGTGGATGGAATAGTGGT
GACTGACATTGACACAATGACAATTGACCCCCAAGTGGAGAAAAAGATGGGACAGGTGCTAC
TCATAGCAGTAGCCGTCTCCAGCGCCATACTGTCGCGGACCGCCTGGGGGTGGGGGGAGGCT
GGGGCCCTGATCACAGCCGCAACTTCCACTTTGTGGGAAGGCTCTCCGAACAAGTACTGGAA
CTCCTCTACAGCCACTTCACTGTGTAACATTTTTAGGGGAAGTTACTTGGCTGGAGCTTCTC
TAATCTACACAGTAACAAGAAACGCTGGCTTGGTCAAGAGACGTGGGGGTGGAACAGGAGAG
ACCCTGGGAGAGAAATGGAAGGCCCGCTTGAACCAGATGTCGGCCCTGGAGTTCTACTCCTA
CAAAAAGTCAGGCATCACCGAGGTGTGCAGAGAAGAGGCCCGCCGCGCCCTCAAGGACGGTG
TGGCAACGGGAGGCCATGCTGTGTCCCGAGGAAGTGCAAAGCTGAGATGGTTGGTGGAGCGG
GGATACCTGCAGCCCTATGGAAAGGTCATTGATCTTGGATGTGGCAGAGGGGCTGGAGTTA
CTACGCCGCCACCATCCGCAAAGTTCAAGAAGTGAAAGGATACACAAAAGGAGGCCCTGGTC
ATGAAGAACCCGTGTTGGTGCAAAGCTATGGGTGGAACATAGTCCGTCTTAAGAGTGGGGTG
GACGTCTTTCATATGGCGGCTGAGCCGTGTGACACGCTGCTGTGTGACATAGGTGAGTCATC
ATCTAGTCCTGAAGTGGAAGAAGCACGGACGCTCAGAGTCCTCTCCATGGTGGGGGATTGGC
TTGAAAAAGACCAGGAGCCTTTTGTATAAAAGTGTTGTGCCCATACACCAGCACTATGATG
GAAACCCTGGAGCGACTGCAGCGTAGGTATGGGGGAGGACTGGTCAGAGTGCCACTCTCCCG
CAACTCTACACATGAGATGTACTGGGTCTCTGGAGCGAAAAGCAACACCATAAAAAGTGTGT
CCACCACGAGCCAGCTCCTCTTGGGGCGCATGGACGGGCCTAGGAGGCCAGTGAAATATGAG
GAGGATGTGAATCTCGGCTCTGGCACGCGGGCTGTGGTAAGCTGCGCTGAAGCTCCCAACAT
GAAGATCATTGGTAACCGCATTGAAAGGATCCGCAGTGAGCACGCGGAAACGTGGTTCTTTG
ACGAGAACCACCCATATAGGACATGGGCTTACCATGGAAGCTATGAGGCCCCCACACAAGGG
TCAGCGTCCTCTCTAATAAACGGGGTTGTCAGGCTCCTGTCAAAACCCTGGGATGTGGTGAC
TGGAGTCACAGGAATAGCCATGACCGACACCACACCGTATGGTCAGCAAAGAGTTTTCAAGG
AAAAAGTGGACACTAGGGTGCCAGACCCCCAAGAAGGCACTCGTCAGGTTATGAGCATGGTC
TCTTCCTGGTTGTGGAAAGAGCTAGGCAAACACAAACGGCCACGAGTCTGTACCAAAGAAGA
GTTCATCAACAAGGTTCGTAGCAATGCAGCATTAGGGGCAATATTTGAAGAGGAAAAAGAGT
GGAAGACTGCAGTGGAAGCTGTGAACGATCCAAGGTTCTGGGCTCTAGTGGACAAGGAAAGA
GAGCACCACCTGAGAGGAGAGTGCCAGAGTTGTGTGTATAACATGATGGGAAAAAGAGAAAA
GAAACAAGGGGAATTTGGAAAGGCCAAGGGCAGCCGCGCCATCTGGTATATGTGGCTAGGGG
CTAGATTTCTAGAGTTCGAAGCCCTTGGATTCTTGAACGAGGATCACTGGATGGGGAGAGAG
AACTCAGGAGGTGGTGTTGAAGGGCTGGATTACAAAGACTCGGATATGTCCTAGAAGAGAT
GAGTCGTATACCAGGAGGAAGGATGTATGCAGATGACACTGCTGGCTGGGACACCCGCATTA
GCAGGTTTGATCTGGAGAATGAAGCTCTAATCACCAACCAAATGGAGAAAGGGCACAGGGCC
TTGGCATTGGCCATAATCAAGTACACATACCAAAACAAAGTGGTAAAGGTCCTTAGACCAGC
TGAAAAAGGGAAAACAGTTATGGACATTATTTCGAGACAAGACCAAAGGGGGAGCGGACAAG
TTGTCACTTACGCTCTTAACACATTTACCAACCTAGTGGTGCAACTCATTCGGAATATGGAG
GCTGAGGAAGTTCTAGAGATGCAAGACTTGTGGCTGCTGCGGAGGTCAGAGAAAGTGACCAA
CTGGTTGCAGAGCAACGGATGGGATAGGCTCAAACGAATGGCAGTCAGTGGAGATGATTGCG
```

-continued

```
TTGTGAAGCCAATTGATGATAGGTTTGCACATGCCCTCAGGTTCTTGAATGATATGGGAAAA

GTTAGAAAGGACACACAAGAGTGGAAACCCTCAACTGGATGGGACAACTGGGAAGAAGTTCC

GTTTTGCTCCCACCACTTCAACAAGCTCCATCTCAAGGACGGGAGGTCCATTGTGGTTCCCT

GCCGCCACCAAGATGAACTGATTGGCCGGGCCCGCGTCTCTCCAGGGGCGGGATGGAGCATC

CGGGAGACTGCTTGCCTAGCAAAATCATATGCGCAGATGTGGCAGCTCCTTTATTTCCACAG

AAGGGACCTCCGACTGATGGCCAATGCCATTTGTTCATCTGTGCCAGTTGACTGGGTTCCAA

CTGGGAGAACTACCTGGTCAATCCATGGAAAGGGAGAATGGATGACCACTGAAGACATGCTT

GTGGTGTGGAACAGAGTGTGGATTGAGGAGAACGACCACATGGAAGACAAGACCCCAGTTAC

GAAATGGACAGACATTCCCTATTTGGGAAAAAGGGAAGACTTGTGGTGTGGATCTCTCATAG

GGCACAGACCGCGCACCACCTGGGCTGAGAACATTAAAAACACAGTCAACATGGTGCGCAGG

ATCATAGGTGATGAAGAAAAGTACATGGACTACCTATCCACCCAAGTTCGCTACTTGGGTGA

AGAAGGGTCTACACCTGGAGTGCTGTAAGCACCAATTTTAGTGTTGTCAGGCCTGCTAGTCA

GCCACAGTTTGGGGAAAGCTGTGCAGCCTGTAACCCCCCAGGAGAAGCTGGGAAACCAAGC

TCATAGTCAGGCCGAGAACGCCATGGCACGGAAGAAGCCATGCTGCCTGTGAGCCCCTCAGA

GGACACTGAGTCAAAAAACCCCACGCGCTTGGAAGCGCAGGATGGGAAAAGAAGGTGGCGAC

CTTCCCCACCCTTCAATCTGGGGCCTGAACTGGAGACTAGCTGTGAATCTCCAGCAGAGGGA

CTAGTGGTTAGAGGAGACCCCCGGAAAACGCAAAACAGCATATTGACGCTGGGAAAGACCA

GAGACTCCATGAGTTTCCACCACGCTGGCCGCCAGGCACAGATCGCCGAACAGCGGCGGCCG

GTGTGGGGAAATCCATGGTTTCT
```

REFERENCES

Throughout this application, various references describe the state of the art to which this invention pertains. The disclosures of these references are hereby incorporated by reference into the present disclosure.

The invention claimed is:

1. A mutant genomic sequence comprising a sequence as set forth in SEQ ID NO:1 in which at least one site of fixation for miR-4279 is restored.

2. The mutant genomic sequence of claim 1 wherein a first site of fixation is restored by substituting the adenosine (A) at position 2707 by a thymine (T), the guanine (G) at position 2713 by an adenosine (A), and the adenosine (A) at position 2716 by a guanine (G).

3. The mutant genomic sequence of claim 1 wherein a second site of fixation is restored by substituting the cytidine (C) at position 3331 by a thymine (T), the cytidine (C) at position 3332 by a thymine (T), and the cytidine (C) at position 3334 by a guanine (G).

4. The mutant genomic sequence of claim 1 wherein a third site of fixation is restored by substituting the guanine (G) at position 5106 by an adenosine (A), the adenosine (A) at position 5113 by a guanine (G), and the adenosine (A) at position 5116 by a guanine (G).

5. The mutant genomic sequence of claim 1 wherein a fourth site of fixation is restored by substituting the cytosine (C) at position 5962 by a thymine (T), and the guanine (G) at position 5971 by an adenosine (A).

6. The mutant genomic sequence of claim 1 wherein a fifth site of fixation is restored by substituting the adenosine (A) at position 6211 by a guanine (G), and the thymine (T) at position 6220 by a cytidine (C).

7. The mutant genomic sequence of claim 1 wherein 1, 2, 3, 4, or 5 sites of fixation are restored in the genomic sequence of the epidemic strain.

8. The mutant genomic sequence of claim 1 which comprises the sequence represented by SEQ ID NO:2.

9. The mutant genomic sequence of claim 1 which encodes for a protein E wherein at least one amino acid residue at position 152, 156 or 158 of the sequence encoding protein E is mutated.

10. The mutant genomic sequence of claim 1 which encodes for a protein E wherein the isoleucine residue (I) at position 152 is substituted by a threonine residue (T), the threonine residue (T) at position 156 is substituted by an isoleucine residue (I), and the histidine residue (H) at position 158 is substituted by a tyrosine residue (Y).

11. The mutant genomic sequence of claim 1 which consists the sequence represented by SEQ ID NO:3.

12. A host cell comprising the mutant genomic sequence of claim 1.

13. An attenuated Zika virus encoded by the mutant genomic sequence of claim 1.

* * * * *

SEQUENCE LISTING

```
<160> NUMBER OF SEQ ID NOS: 9

<210> SEQ ID NO 1
<211> LENGTH: 10727
<212> TYPE: DNA
<213> ORGANISM: Artificial Sequence
<220> FEATURE:
<223> OTHER INFORMATION: Synthetic Genomic sequence of parental
      ZIKVBR15-MC BeH819015 (10,727 nt)

<400> SEQUENCE: 1
tgtgaatcag actgcgacag ttcgagtttg aagcgaaagc tagcaacagt atcaacaggt      60
tttattttgg atttggaaac gagagtttct ggtcatgaaa acccaaaaa agaaatccgg      120 aggattccgg attgtcaata tgctaaaacg cggagtagcc cgtgtgagcc cctttggggg    180
cttgaagagg ctgccagccg gacttctgct gggtcatggg cccatcagga tggtcttggc    240
gattctagcc tttttgagat tcacggcaat caagccatca ctgggtctca tcaatagatg    300
gggttcagtt gggaaaaaag aggctatgga ataataaag aagttcaaga aagatctggc    360
tgccatgctg agaataatca atgctaggaa ggagaagaag agacgaggcg cagatactag    420
tgtcggaatt gttggcctcc tgctgaccac agctatggca gcggaggtca ctagacgtgg    480
gagtgcatac tatatgtact tggacagaaa cgatgctggg gaggccatat cttttccaac    540
```

```
cacattgggg atgaataagt gttatataca gatcatggat cttggacaca tgtgtgatgc     600
caccatgagc tatgaatgcc ctatgctgga tgagggggtg gaaccagatg acgtcgattg     660
ttggtgcaac acgacgtcaa cttgggttgt gtacggaacc tgccatcaca aaaaggtga      720
agcacggaga tctagaagag ctgtgacgct cccctcccat tccactagga agctgcaaac     780
gcggtcgcaa acctggttgg aatcaagaga atacacaaag cacttgatta gagtcgaaaa     840
ttggatattc aggaaccctg gcttcgcgtt agcagcagct gccatcgctt ggcttttggg     900
aagctcaacg agccaaaaag tcatatactt ggtcatgata ctgctgattg ccccggcata     960
cagcatcagg tgcataggag tcagcaatag ggactttgtg aaggtatgt caggtgggac     1020
ttgggttgat gttgtcttgg aacatggagg ttgtgtcacc gtaatggcac aggacaaacc     1080
gactgtcgac atagagctgg ttacaacaac agtcagcaac atggcggagg taagatccta     1140
ctgctatgag gcatcaatat cagacatggc ttcggacagc cgctgcccaa cacaaggtga     1200
agcctacctt gacaagcaat cagacactca atatgtctgc aaaagaacgt tagtggacag     1260
aggctgggga atggatgtg actttttggg caaaggagc ctggtgacat gcgctaagtt       1320
tgcatgctcc aagaaaatga ccgggaagag catccagcca gagaatctgg agtaccggat     1380
aatgctgtca gttcatggct cccagcacag tgggatgatc gttaatgaca caggacatga     1440
aactgatgag aatagagcga aagttgagat aacgcccaat tcaccaagag ccgaagccac     1500
cctgggggt tttggaagcc taggacttga ttgtgaaccg gacaggcc ttgacttttc        1560
agatttgtat tacttgacta tgaataacaa gcactggttg gttcacaagg agtggttcca    1620
cgacattcca ttaccttggc acgctggggc agacaccgga actccacact ggaacaacaa     1680
agaagcactg gtagagttca aggacgcaca tgccaaaagg caaactgtcg tggttctagg    1740
gagtcaagaa ggagcagttc acacggccct tgctggagct ctggaggctg agatggatgg    1800
tgcaaaggga aggctgtcct ctggccactt gaaatgtcgc ctgaaaatgg ataaacttag    1860
attgaagggc gtgtcatact ccttgtgtac tgcagcgttc acattcacca agatcccggc    1920
tgaaacactg cacgggacag tcacagtgga ggtacagtac gcagggacag atggaccttg    1980
caaggttcca gctcagatgg cggtggacat gcaaactctg acccagttg ggaggttgat     2040
aaccgctaac cccgtaatca ctgaaagcac tgagaactct aagatgatgc tggaacttga    2100
tccaccattt ggggactctt acattgtcat aggagtcggg gagaagaaga tcacccacca    2160
ctggcacagg agtggcagca ccattggaaa agcatttgaa gccactgtga gaggtgccaa    2220
gagaatggca gtcttgggag acacagcctg gacttgga tcagttggag gcgctctcaa      2280
ctcattgggc aagggcatcc atcaaatttt tggagcagct ttcaaatcat tgtttggagg    2340
aatgtcctgg ttctcacaaa ttctcattgg aacgttgctg atgtggttgg gtctgaacac    2400
aaaagaatgga tctatttccc ttatgtgctt ggccttaggg ggggtgttga tcttcttatc   2460
cacagccgtc tctgctgatg tggggtgctc ggtggacttc tcaaagaagg agacgagatg    2520
cggtacaggg gtgttcgtct ataacgacgt tgaagcctgg agggacaggt acaagtacca    2580
tcctgactcc ccccgtagat tggcagcagc agtcaagcaa gcctgggaag atggtatctg    2640
cgggatctcc tctgtttcaa gaatggaaaa catcatgtgg agatcagtag aaggggagct    2700
caacgcaatc ctggaagaga atggagttca actgacggtc gttgtgggat ctgtaaaaaa    2760
ccccatgtgg agaggtccac agagattgcc cgtgcctgtg aacgagctgc ccacggctg     2820
gaaggcttgg gggaaatcgt acttcgtcag agcagcaaag acaaataaca gcttgtcgt     2880
ggatggtgac acactgaagg aatgcccact caaacataga gcatggaaca gctttcttgt    2940
```

```
ggaggatcat gggttcgggg tatttcacac tagtgtctgg ctcaaggtta gagaagatta   3000
ttcattagag tgtgatccag ccgttattgg aacagctgtt aagggaaagg aggctgtaca   3060
cagtgatcta ggctactgga ttgagagtga aagaatgac acatggaggc tgaagagggc    3120
ccatctgatc gagatgaaaa catgtgaatg gccaaagtcc cacacattgt ggacagatgg   3180
aatagaagag agtgatctga tcatacccaa gtctttagct gggccactca gccatcacaa   3240
taccagagag ggctacagga cccaaatgaa agggccatgg cacagtgaag agcttgaaat   3300
tcggtttgag gaatgcccag gcactaaggt ccacgtggag gaaacatgtg aacaagagg    3360
accatctctg agatcaacca ctgcaagcgg aagggtgatc gaggaatggt gctgcaggga   3420
gtgcacaatg cccccactgt cgttccgggc taaagatggc tgttggtatg aatggagat    3480
aaggcccagg aaagaaccag aaagcaactt agtaaggtca atggtgactg caggatcaac   3540
tgatcacatg gaccacttct cccttggagt gcttgtgatc ctgctcatgg tgcaggaagg   3600
gctgaagaag agaatgacca caaagatcat cataagcaca tcaatggcag tgctggtagc   3660
tatgatcctg ggaggatttt caatgagtga cctggctaag cttgcaattt tgatgggtgc   3720
caccttcgcg gaaatgaaca ctggaggaga tgtagctcat ctggcgctga tagcggcatt   3780
caaagtcaga ccagcgttgc tggtatcttt catcttcaga gctaattgga caccccgtga   3840
aagcatgctg ctggccttgg cctcgtgtct tttgcaaact gcgatctccg ccttggaagg   3900
cgacctgatg gttctcatca atggttttgc tttggcctgg ttggcaatac gagcgatggt   3960
tgttccacgc actgataaca tcaccttggc aatcctggct gctctgacac cactggcccg   4020
gggcacactg cttgtggcgt ggagagcagg ccttgctact tgcggggggt ttatgctcct   4080
ctctctgaag ggaaaaggca gtgtgaagaa gaacttacca tttgtcatgg ccctgggact   4140
aaccgctgtg aggctggtcg acccccatcaa cgtggtggga ctgctgttac tcacaaggag   4200
tgggaagcgg agctggcccc ctagcgaagt actcacagct gttggcctga tatgcgcatt   4260
ggctggaggg ttcgccaagg cagatataga gatggctggg cccatggccg cggtcggtct   4320
gctaattgtc agttacgtgg tctcaggaaa gagtgtggac atgtacattg aaagagcagg   4380
tgacatcaca tgggaaaaag atgcggaagt cactggaaac agtcccccggc tcgatgtggc   4440
gctagatgag agtggtgatt tctccctggt ggaggatgac ggtcccccca tgagagagat   4500
catactcaag gtggtcctga tgaccatctg tggcatgaat ccaatagcca tacccttgc    4560
agctggagcg tggtacgtat acgtgaagac tggaaaaagg agtggtgctc tatgggatgt   4620
gcctgctccc aaggaagtaa aaaagggga gaccacagat ggagtgtaca gagtaatgac   4680
tcgtagactg ctaggttcaa cacaagttgg agtgggagtt atgcaagagg gggtctttca   4740
cactatgtgg cacgtcacaa aaggatccgc gctgagaagc ggtgaaggga acttgatcc    4800
atactgggga gatgtcaagc aggatctggt gtcatactgt ggtccatgga agctagatgc   4860
cgcctgggac gggcacagcg aggtgcagct cttggccgtg ccccccggag agagagcgag   4920
gaacatccag actctgcccg gaatatttaa gacaaaggat ggggacattg gagcggttgc   4980
gctggattac ccagcaggaa cttcaggatc tccaatccta gacaagtgtg ggagagtgat   5040
aggactttat ggcaatgggg tcgtgatcaa aaatggagag tatgttagtg ccatcaccca   5100
agggaggagg gaagaagaga ctcctgttga gtgcttcgag ccctcgatgc tgaagaagaa   5160
gcagctaact gtcttagact tgcatcctgg agctgggaaa accaggagag ttcttcctga   5220
aatagtccgt gaagccataa aaacaagact ccgtactgtg atcttagctc aaccagggt    5280
tgtcgctgct gaaatggagg aggcccttag agggcttcca gtgcgttata tgacaacagc   5340
```

```
agtcaatgtc acccactctg gaacagaaat cgtcgactta atgtgccatg ccaccttcac   5400
ttcacgtcta ctacagccaa tcagagtccc caactataat ctgtatatta tggatgaggc   5460
ccacttcaca gatccctcaa gtatagcagc aagaggatac atttcaacaa gggttgagat   5520
gggcgaggcg gctgccatct tcatgaccgc cacgccacca ggaacccgtg acgcatttcc   5580
ggactccaac tcaccaatta tggacaccga agtggaagtc ccagagagag cctggagctc   5640
aggctttgat tgggtgacgg atcattctgg aaaaacagtt tggtttgttc caagcgtgag   5700
gaacggcaat gagatcgcag cttgtctgac aaaggctgga aaacgggtca tacagctcag   5760
cagaaagact tttgagacag agttccagaa aacaaaacat caagagtggg actttgtcgt   5820
gacaactgac atttcagaga tgggcgccaa ctttaaagct gaccgtgtca tagattccag   5880
gagatgccta aagccggtca tacttgatgg cgagagagtc attctggctg acccatgcc   5940
tgtcacacat gccagcgctg cccagaggag ggggcgcata ggcaggaatc ccaacaaacc   6000
tggagatgag tatctgtatg gaggtggggtg cgcagagact gacgaagacc atgcacactg   6060
gcttgaagca agaatgctcc ttgacaatat ttacctccaa gatggcctca tagcctcgct   6120
ctatcgacct gaggccgaca aagtagcagc cattgaggga gagttcaagc ttaggacgga   6180
gcaaaggaag acctttgtgg aactcatgaa agaggagat cttcctgttt ggctggccta   6240
tcaggttgca tctgccggaa taacctacac agatagaaga tggtgctttg atggcacgac   6300
caacaacacc ataatggaag atagtgtgcc ggcagaggtg tggaccagac acggagagaa   6360
aagagtgctc aaaccgaggt ggatggacgc cagagtttgt tcagatcatg cggccctgaa   6420
gtcattcaag gagtttgccg ctgggaaaag aggagcggtc tttggagtga tggaagccct   6480
gggaacactg ccaggacaca tgacagagag attccaggaa gccattgaca acctcgctgt   6540
gctcatgcgg gcagagactg gaagcaggcc ttacaaagcc gcggcggccc aattgccgga   6600
gaccctagag accataatgc ttttgggggtt gctgggaaca gtctcgctgg gaatcttctt   6660
cgtcttgatg aggaacaagg gcataggga gatgggctt ggaatggtga ctcttggggc   6720
cagcgcatgg ctcatgtggc tctcggaaat tgagccagcc agaattgcat gtgtcctcat   6780
tgttgtgttc ctattgctgg tggtgctcat acctgagcca gaaaagcaaa gatctcccca   6840
ggacaaccaa atggcaatca tcatcatggt agcagtaggt cttctgggct tgattaccgc   6900
caatgaactc ggatggttgg agagaacaaa gagtgaccta agccatctaa tgggaaggag   6960
agaggagggg gcaaccatag gattctcaat ggacattgac ctgcggccag cctcagcttg   7020
ggccatctat gctgccttga aactttcat taccccagcc gtccaacatg cagtgaccac   7080
ctcatacaac aactactcct taatggcgat ggccacgcaa gctggagtgt tgtttggtat   7140
gggcaaaggg atgccattct acgcatggga ctttggagtc ccgctgctaa tgataggttg   7200
ctactcacaa ttaacacccc tgaccctaat agtggccatc attttgctcg tggcgcacta   7260
catgtacttg atcccagggc tgcaggcagc agctgcgcgt gctgcccaga gagaacggc   7320
agctggcatc atgaagaacc tgttgtgga tggaatagtg gtgactgaca ttgacacaat   7380
gacaattgac ccccaagtgg agaaaaagat gggacaggtg ctactcatag cagtagccgt   7440
ctccagcgcc atactgtcgc ggaccgcctg ggggtgggg gaggctgggg ccctgatcac   7500
agccgcaact tccactttgt gggaaggctc tccgaacaag tactggaact cctctacagc   7560
cacttcactg tgtaacattt ttaggggaag ttacttggct ggagcttctc taatctacac   7620
agtaacaaga aacgctggct tggtcaagag acgtggggt ggaacaggag agaccctggg   7680
agagaaatgg aaggcccgct tgaaccagat gtcggccctg gagttctact cctacaaaaa   7740
```

```
gtcaggcatc accgaggtgt gcagagaaga ggcccgccgc gccctcaagg acggtgtggc    7800
aacgggaggc catgctgtgt cccgaggaag tgcaaagctg agatggttgg tggagcgggg    7860
atacctgcag ccctatggaa aggtcattga tcttggatgt ggcagagggg gctggagtta    7920
ctacgccgcc accatccgca aagttcaaga agtgaaagga tacacaaaag gagggccctgg  7980
tcatgaagaa cccgtgttgg tgcaaagcta tgggtggaac atagtccgtc ttaagagtgg    8040
ggtggacgtc tttcatatgg cggctgagcc gtgtgacacg ctgctgtgtg acataggtga    8100
gtcatcatct agtcctgaag tggaagaagc acggacgctc agagtcctct ccatggtggg    8160
ggattggctt gaaaaaagac caggagcctt ttgtataaaa gtgttgtgcc catacaccag    8220
cactatgatg gaaaccctgg agcgactgca gcgtaggtat gggggaggac tggtcagagt    8280
gccactctcc cgcaactcta cacatgagat gtactgggtc tctggagcga aaagcaacac    8340
cataaaaagt gtgtccacca cgagccagct cctcttgggg cgcatggacg ggcctaggag    8400
gccagtgaaa tatgaggagg atgtgaatct cggctctggc acgcgggctg tggtaagctg    8460
cgctgaagct cccaacatga agatcattgg taaccgcatt gaaaggatcc gcagtgagca    8520
cgcggaaacg tggttctttg acgagaacca cccatatagg acatgggctt accatggaag    8580
ctatgaggcc cccacacaag ggtcagcgtc ctctctaata aacggggttg tcaggctcct    8640
gtcaaaccc tgggatgtgg tgactggagt cacaggaata gccatgaccg acaccacacc      8700
gtatggtcag caaagagttt tcaaggaaaa agtggacact agggtgccag ccccccaaga     8760
aggcactcgt caggttatga gcatggtctc ttcctggttg tggaaagagc taggcaaaca     8820
caaacggcca cgagtctgta ccaaagaaga gttcatcaac aaggttcgta gcaatgcagc     8880
attaggggca atatttgaag aggaaaaaga gtggaagact gcagtggaag ctgtgaacga     8940
tccaaggttc tgggctctag tggacaagga aagagagcac cacctgagag agagtgccaa    9000
gagttgtgtg tataacatga tgggaaaaag agaaaagaaa caagggaat ttggaaaggc    9060
caagggcagc cgcgccatct ggtatatgtg gctaggggct agatttctag agttcgaagc    9120
ccttggattc ttgaacgagg atcactggat ggggagagag aactcaggag gtggtgttga    9180
agggctggga ttacaaagac tcggatatgt cctagaagat atgagtcgta taccaggagg    9240
aaggatgtat gcagatgaca ctgctggctg ggacacccgc attagcaggt ttgatctgga    9300
gaatgaagct ctaatcacca accaaatgga gaaaggcac agggccttgg cattggccat     9360
aatcaagtac atacccaaa acaaagtggt aaaggtcctt agaccagctg aaaaagggaa      9420
aacagttatg gacattattt cgagacaaga ccaaaggggg agcggacaag ttgtcactta     9480
cgctcttaac acatttacca acctagtggt gcaactcatt cggaatatgg aggctgagga    9540
agttctagag atgcaagact tgtggctgct gcggaggtca gagaaagtga ccaactggtt    9600
gcagagcaac ggatgggata ggctcaaacg aatggcagtc agtggagatg attgcgttgt    9660
gaagccaatt gatgataggt ttgcacatgc cctcaggttc ttgaatgata tgggaaaagt    9720
tagaaaggac acacaagagt ggaaaccctc aactggatgg acaactggg aagaagttcc     9780
gttttgctcc caccacttca caagctccat ctctcaaggac gggaggtcca ttgtggttcc    9840
ctgccgccac caagatgaac tgattggccg ggcccgcgtc tctccagggg cgggatggag    9900
catccgggag actgcttgcc tagcaaaatc atatgcgcag atgtggcagc tcctttattt    9960
ccacagaagg gacctccgac tgatggccaa tgccatttgt tcatctgtgc cagttgactg   10020
ggttccaact gggagaacta cctggtcaat ccatggaaag ggagaatgga tgaccactga  10080
agacatgctt gtggtgtgga acagagtgtg gattgaggag aacgaccaca tggaagacaa   10140
```

-continued

| | |
|---|---|
| gaccccagtt acgaaatgga cagacattcc ctatttggga aaaagggaag acttgtggtg | 10200 |
| tggatctctc ataggggcaca daccgcgcac cacctgggct gagaacatta aaaacacagt | 10260 |
| caacatggtg cgcaggatca taggtgatga agaaaagtac atggactacc tatccaccca | 10320 |
| agttcgctac ttgggtgaag aagggtctac acctggagtg ctgtaagcac caatcttaat | 10380 |
| gttgtcaggc ctgctagtca gccacagctt ggggaaagct gtgcagcctg tgaccccca | 10440 |
| ggagaagctg ggaaaccaag cctatagtca ggccgagaac gccatggcac ggaagaagcc | 10500 |
| atgctgcctg tgagcccctc agaggatact gagtcaaaaa accccacgcg cttggaggcg | 10560 |
| caggatggga aaagaaggtg gcgaccttcc ccaccttca atctggggcc tgaactggag | 10620 |
| atcagctgtg gatccccaga gagggacta gtggttagag gagacccccc ggaaaacgca | 10680 |
| aaacagcata ttgacgctgg gaaagaccag agactccatg agtttcc | 10727 |

<210> SEQ ID NO 2
<211> LENGTH: 10807
<212> TYPE: DNA
<213> ORGANISM: Artificial Sequence
<220> FEATURE:
<223> OTHER INFORMATION: Synthetic Genomic sequence of chimeric
      ZIKVBR15-MC mutant miR4279 (10,807 nt)

<400> SEQUENCE: 2

| | |
|---|---|
| agttgttgat ctgtgtgagt cagactgcga cagttcgagt ctgaagcgag agctaacaac | 60 |
| agtatcaaca ggtttaattt ggatttggaa acgagagttt ctggtcatga aaaacccaaa | 120 |
| aaagaaatcc ggaggattcc ggattgtcaa tatgctaaaa cgcggagtag cccgtgtgag | 180 |
| cccctttggg ggcttgaaga ggctgccagc cggacttctg ctgggtcatg ggcccatcag | 240 |
| gatggtcttg gcgattctag ccttttttgag attcacggca atcaagccat cactgggtct | 300 |
| catcaataga tggggttcag ttgggaaaaa agaggctatg gaaataataa gaagttcaa | 360 |
| gaaagatctg gctgccatgc tgagaataat caatgctagg aaggagaaga gagacgagg | 420 |
| cgcagatact agtgtcggaa ttgttggcct cctgctgacc acagctatgg cagcggaggt | 480 |
| cactagacgt gggagtgcat actatatgta cttggacaga aacgatgctg gggaggccat | 540 |
| atcttttcca accacattgg ggatgaataa gtgttatata cagatcatgg atcttggaca | 600 |
| catgtgtgat gccaccatga gctatgaatg ccctatgctg gatgagggg tggaaccaga | 660 |
| tgacgtcgat tgttggtgca acacgacgtc aacttgggtt gtgtacggaa cctgccatca | 720 |
| caaaaaggt gaagcacgga gatctagaag agctgtgacg ctcccctccc attccactag | 780 |
| gaagctgcaa acgcggtcgc aaacctggtt ggaatcaaga gaatacacaa agcacttgat | 840 |
| tagagtcgaa aattggatat tcaggaaccc tggcttcgcg ttagcagcag ctgccatcgc | 900 |
| ttggcttttg ggaagctcaa cgagccaaaa agtcatatac ttggtcatga tactgctgat | 960 |
| tgccccggca tacagcatca ggtgcatagg agtcagcaat agggactttg tggaaggtat | 1020 |
| gtcaggtggg acttgggttg atgttgtctt ggaacatgga ggttgtgtca ccgtaatggc | 1080 |
| acaggacaaa ccgactgtcg acatagagct ggttacaaca acagtcagca acatggcgga | 1140 |
| ggtacgatcg tactgctatg aggcatcaat atcagacatg gcttcggaca gccgctgccc | 1200 |
| aacacaaggt gaagcctacc ttgacaagca atcagacact caatatgtct gcaaaagaac | 1260 |
| gttagtggac agaggctggg gaaatggatg tggacttttt ggcaaaggga gcctggtgac | 1320 |
| atgcgctaag tttgcatgct ccaagaaaat gaccgggaag agcatccagc cagagaatct | 1380 |
| ggagtaccgg ataatgctgt cagttcatgg ctcccagcac agtgggatga tcgttaatga | 1440 |

```
cacaggacat gaaactgatg agaatagagc gaaagttgag ataacgccca attcaccaag    1500
agccgaagcc accctggggg gttttggaag cctaggactt gattgtgaac cgaggacagg    1560
ccttgacttt tcagatttgt attacttgac tatgaataac aagcactggt tggttcacaa    1620
ggagtggttc cacgcacatt cattaccttg gcacgctggg gcagacaccg gaactccaca    1680
ctggaacaac aaagaagcac tggtagagtt caaggacgca catgccaaaa ggcaaactgt    1740
cgtggttcta gggagtcaag aaggagcagt tcacacggcc cttgctggag ctctggaggc    1800
tgagatggat ggtgcaaagg gaaggctgtc ctctggccac ttgaaatgtc gcctgaaaat    1860
ggataaactt agattgaagg gcgtgtcata ctccttgtgt actgcagcgt tcacattcac    1920
caagatcccg gctgaaacac tgcacgggac agtcacagtg gaggtacagt acgcagggac    1980
agatggacct tgcaaggttc cagctcagat ggcggtggac atgcaaactc tgacccagt    2040 tgggaggttg ataaccgcta accccgtaat cactgaaagc actgagaact ctaagatgat    2100
gctggaactt gatccaccat ttggggactc ttacattgtc ataggagtcg gggagaagaa    2160
gatcacccac cactggcaca ggagtggcag caccattgga aaagcatttg aggccactgt    2220
gagaggcgcc aagagaatgg cagtcctggg ggacacagcc tgggactttg atcagttgg    2280 aggcgctctc aactcattgg gcaagggcat ccatcaaatt tttggagcag ctttcaaatc    2340
attgtttgga ggaatgtcct ggttctcaca aattctcatt ggaacgttgc tgatgtggtt    2400
gggtctgaac acaaagaatg gatctatttc ccttatgtgc ttggccttag ggggggtgtt    2460
gatcttctta tccacagccg tctctgctga tgtggggtgc tcggtggact tctcaaagaa    2520
ggagacgaga tgcggtacag gggtgttcgt ctataacgac gttgaagcct ggagggacag    2580
gtacaagtac catcctgact cccccgtag attggcagca gcagtcaagc aagcctggga    2640
agatggtatc tgcgggatct cctctgtttc aagaatggaa acatcatgt ggagatcagt    2700 agaaggggag ctcaacgcta tcctagagga gaatggagtt caactgacgg tcgttgtggg    2760
atctgtaaaa aaccccatgt ggagaggtcc acagagattg cccgtgcctg tgaacgagct    2820
gccccacggc tggaaggctt gggggaaatc gtacttcgtc agagcagcaa agacaaataa    2880
cagctttgtc gtggatggtg acacactgaa ggaatgccca ctcaaacata gagcatggaa    2940
cagctttctt gtggaggatc atgggttcgg ggtatttcac actagtgtct ggctcaaggt    3000
tagagaagat tattcattag agtgtgatcc agccgttatt ggaacagctg ttaagggaaa    3060
ggaggctgta cacagtgatc taggctactg gattgagagt gagaagaatg acacatggag    3120
gctgaagagg gcccatctga tcgagatgaa aacatgtgaa tggccaaagt cccacacatt    3180
gtggacagat ggaatagaag agagtgatct gatcataccc aagtctttag ctgggccact    3240
cagccatcac aataccagag agggctacag gacccaaatg aaaggccat ggcacagtga    3300 agagcttgaa attcggtttg aggaatgccc aggcactaag gtttacgtgg aggagacatg    3360
tggaacaaga ggaccatctc tgagatcaac cactgcaagc ggaagggtga tcgaggaatg    3420
gtgctgcagg gagtgcacaa tgcccccact gtcgttccgg gctaaagatg ctgttggta    3480 tggaatggag ataaggccca ggaaagaacc agaaagcaac ttagtaaggt caatggtgac    3540
tgcaggatca actgatcaca tggaccactt ctcccttgga gtgcttgtga tcctgctcat    3600
ggtgcaggaa gggctgaaga agagaatgac cacaaagatc atcataagca catcaatggc    3660
agtgctggta gctatgatcc tgggaggatt tcaatgagt gacctggcta agcttgcaat    3720
tttgatgggt gccaccttcg cggaaatgaa cactggagga gatgtagctc atctggcgct    3780
gatagcggca ttcaaagtca gaccagcgtt gctggtatct ttcatcttca gagctaattg    3840
```

-continued

```
gacaccccgt gaaagcatgc tgctggcctt ggcctcgtgt cttttgcaaa ctgcgatctc    3900
cgccttggaa ggcgacctga tggttctcat caatggtttt gctttggcct ggttggcaat    3960
acgagcgatg gttgttccac gcactgataa catcaccttg gcaatcctgg ctgctctgac    4020
accactggcc cggggcacac tgcttgtggc gtggagagca ggccttgcta cttgcggggg    4080
gtttatgctc ctctctctga agggaaaagg cagtgtgaag aagaacttac catttgtcat    4140
ggccctggga ctaaccgctg tgaggctggt cgaccccatc aacgtggtgg gactgctgtt    4200
actcacaagg agtgggaagc ggagctggcc ccctagcgaa gtactcacag ctgttggcct    4260
gatatgcgca ttggctggag ggttcgccaa ggcagatata gagatggctg ggcccatggc    4320
cgcggtcggt ctgctaattg tcagttacgt ggtctcagga aagagtgtgg acatgtacat    4380
tgaaagagca ggtgacatca catgggaaaa agatgcggaa gtcactggaa acagtccccg    4440
gctcgatgtg gcgctagatg agagtggtga tttctccctg gtggaggatg acggtccccc    4500
catgagagag atcatactca aggtggtcct gatgaccatc tgtggcatga atccaatagc    4560
cataccctt gcagctggag cgtggtacgt atacgtgaag actggaaaaa ggagtggtgc    4620
tctatgggat gtgcctgctc ccaaggaagt aaaaaagggg gagaccacag atggagtgta    4680
cagagtaatg actcgtagac tgctaggttc aacacaagtt ggagtgggag ttatgcaaga    4740
gggggtcttt cacactatgt ggcacgtcac aaaaggatcc gcgctgagaa gcggtgaagg    4800
gagacttgat ccatactggg gagatgtcaa gcaggatctg gtgtcatact gtggtccatg    4860
gaagctagat gccgcctggg acgggcacag cgaggtgcag ctcttggccg tgccccccgg    4920
agagagagcg aggaacatcc agactctgcc cggaatattt aagacaaagg atggggacat    4980
tggagcggtt gcgctggatt acccagcagg aacttcagga tctccaatcc tagacaagtg    5040
tgggagagtg ataggacttt atggcaatgg ggtcgtgatc aaaaatggga gttatgttag    5100
tgccatcacc caagggaaga gggaggagga gactcctgtt gagtgcttcg agccctcgat    5160
gctgaagaag aagcagctaa ctgtcttaga cttgcatcct ggagctggga aaaccaggag    5220
agttcttcct gaaatagtcc gtgaagccat aaaaacaaga ctccgtactg tgatcttagc    5280
tccaaccagg gttgtcgctg ctgaaatgga ggaggccctt agagggcttc cagtgcgtta    5340
tatgacaaca gcagtcaatg tcacccactc tggaacagaa atcgtcgact taatgtgcca    5400
tgccaccttc acttcacgtc tactacagcc aatcagagtc cccaactata atctgtatat    5460
tatggatgag gcccacttca cagatccctc aagtatagca gcaagaggat acatttcaac    5520
aagggttgag atgggcgagg cggctgccat cttcatgacc gccacgccac caggaaccccg    5580
tgacgcattt ccggactcca actcaccaat tatggacacc gaagtggaag tcccagagag    5640
agcctggagc tcaggctttg attgggtgac ggatcattct ggaaaaacag tttggttttgt    5700
tccaagcgtg aggaacggca atgagatcgc agcttgtctg acaaaggctg gaaaacgggt    5760
catacagctc agcagaaaga cttttgagac agagttccag aaaacaaaac atcaagagtg    5820
ggactttgtc gtgacaactg acatttcaga gatgggcgcc aactttaaag ctgaccgtgt    5880
catagattcc aggagatgcc taaagccggt catacttgat ggcgagagag tcattctggc    5940
tggacccatg cctgtcacac atgccagcgc tgctcagagg agagggcgca taggcaggaa    6000
tcccaacaaa cctggagatg agtatctgta tggaggtggg tgcgcagaga ctgacgaaga    6060
ccatgcacac tggcttgaag caagaatgct ccttgacaat atttacctcc aagatggcct    6120
catagcctcg ctctatcgac ctgaggccga caaagtagca gccattgagg gagagttcaa    6180
gcttaggacg gagcaaagga agaccctttg tggaactcatg aagagaggag accttcctgt    6240
```

```
ttggctggcc tatcaggttg catctgccgg aataacctac acagatagaa gatggtgctt    6300
tgatggcacg accaacaaca ccataatgga agatagtgtg ccggcagagg tgtggaccag    6360
acacggagag aaaagagtgc tcaaaccgag gtggatggac gccagagttt gttcagatca    6420
tgcggccctg aagtcattca aggagtttgc cgctgggaaa agaggagcgg cttttggagt    6480
gatggaagcc ctgggaacac tgccaggaca catgacagag agattccagg aagccattga    6540
caacctcgct gtgctcatgc gggcagagac tggaagcagg ccttacaaag ccgcggcggc    6600
ccaattgccg gagaccctag agaccataat gcttttgggg ttgctgggaa cagtctcgct    6660
gggaatcttc ttcgtcttga tgaggaacaa gggcataggg aagatgggct ttggaatggt    6720
gactcttggg gccagcgcat ggctcatgtg gctctcggaa attgagccag ccagaattgc    6780
atgtgtcctc attgttgtgt tcctattgct ggtggtgctc atacctgagc cagaaaagca    6840
aagatctccc caggacaacc aaatggcaat catcatcatg gtagcagtag tcttctgggg    6900
cttgattacc gccaatgaac tcggatggtt ggagagaaca aagagtgacc taagccatct    6960
aatgggaagg agagaggagg gggcaaccat aggattctca atggacattg acctgcggcc    7020
agcctcagct tgggccatct atgctgcctt gacaactttc attaccccag ccgtccaaca    7080
tgcagtgacc acttcataca acaactactc cttaatggcg atggccacgc aagctggagt    7140
gttgtttggt atgggcaaag ggatgccatt ctacgcatgg gactttggag tcccgctgct    7200
aatgataggt tgctactcac aattaacacc cctgaccta atagtggcca tcattttgct    7260
cgtggcgcac tacatgtact tgatcccagg gctgcaggca gcagctgcgc gtgctgccca    7320
gaagagaacg gcagctggca tcatgaagaa ccctgttgtg gatggaatag tggtgactga    7380
cattgacaca atgacaattg accccaagt ggagaaaaag atgggacagg tgctactcat    7440
agcagtagcc gtctccagcg ccatactgtc gcggaccgcc tggggtggg gggaggctgg    7500 ggccctgatc acagccgcaa cttccacttt gtgggaaggc tctccgaaca agtactggaa    7560
ctcctctaca gccacttcac tgtgtaacat ttttagggga agttacttgg ctggagcttc    7620
tctaatctac acagtaacaa gaaacgctgg cttggtcaag agacgtgggg gtggaacagg    7680
agagaccctg ggagagaaat ggaaggcccg cttgaaccag atgtcggccc tggagttcta    7740
ctcctacaaa aagtcaggca tcaccgaggt gtgcagagaa gaggcccgcc gcgccctcaa    7800
ggacggtgtg gcaacgggag gccatgctgt gtcccgagga agtgcaaagc tgagatggtt    7860
ggtggagcgg ggatacctgc agccctatgg aaaggtcatt gatcttggat gtggcagagg    7920
gggctggagt tactacgccg ccaccatccg caaagttcaa gaagtgaaag gatacacaaa    7980
aggaggccct ggtcatgaag aacccgtgtt ggtgcaaagc tatgggtgga acatagtccg    8040
tcttaagagt ggggtggacg tctttcatat ggcggctgag ccgtgtgaca cgctgctgtg    8100
tgacataggt gagtcatcat ctagtcctga agtggaagaa gcacggacgc tcagagtcct    8160
ctccatggtg ggggattggc ttgaaaaaag accaggagcc ttttgtataa aagtgttgtg    8220
cccatacacc agcactatga tggaaaccct ggagcgactg cagcgtaggt atggggagg    8280 actggtcaga gtgccactct cccgcaactc tacacatgag atgtactggg tctctggagc    8340
gaaaagcaac accataaaaa gtgtgtccac cacgagccag ctcctcttgg ggcgcatgga    8400
cgggcctagg aggccagtga atatgaggac ggatgtgaat ctcggctctg gcacgcgggc    8460
tgtggtaagc tgcgctgaag ctcccaacat gaagatcatt ggtaaccgca ttgaaaggat    8520
ccgcagtgag cacgcggaaa cgtggttctt tgacgagaac cacccatata ggacatgggc    8580
ttaccatgga agctatgagg cccccacaca agggtcagcg tcctctctaa taaacggggt    8640
```

-continued

```
tgtcaggctc ctgtcaaaac cctgggatgt ggtgactgga gtcacaggaa tagccatgac    8700
cgacaccaca ccgtatggtc agcaaagagt tttcaaggaa aaagtggaca ctagggtgcc    8760
agaccccaa gaaggcactc gtcaggttat gagcatggtc tcttcctggt tgtggaaaga    8820
gctaggcaaa cacaaacggc cacgagtctg taccaaagaa gagttcatca acaaggttcg    8880
tagcaatgca gcattagggg caatatttga agaggaaaaa gagtggaaga ctgcagtgga    8940
agctgtgaac gatccaaggt tctgggctct agtggacaag gaaagagagc accacctgag    9000
aggagagtgc cagagttgtg tgtataacat gatgggaaaa agagaaaaga aacaagggga    9060
atttggaaag gccaagggca gccgcgccat ctggtatatg tggctagggg ctagattcct    9120
agagttcgaa gcccttggat tcttgaacga ggatcactgg atggggagag agaactcagg    9180
aggtggtgtt gaagggctgg gattacaaag actcggatat gtcctagaag agatgagtcg    9240
tataccagga ggaaggatgt atgcagatga cactgctggc tgggacaccc gcattagcag    9300
gtttgatctg gagaatgaag ctctaatcac caaccaaatg gagaaaggggc acagggcctt    9360
ggcattggcc ataatcaagt acacatacca aaacaaagtg gtaaaggtcc ttagaccagc    9420
tgaaaaaggg aaaacagtta tggacattat ttcgagacaa gaccaaaggg ggagcggaca    9480
agttgtcact tacgctctta acacatttac caacctagtg gtgcaactca ttcggaatat    9540
ggaggctgag gaagttctag agatgcaaga cttgtggctg ctgcggaggt cagagaaagt    9600
gaccaactgg ttgcagagca cggatgggga taggctcaaa cgaatggcag tcagtggaga    9660
tgattgcgtt gtgaagccaa ttgatgatag gttttgcacat gccctcaggt tcttgaatga    9720
tatgggaaaa gttagaaagg acacacaaga gtggaaaccc tcaactggat gggacaactg    9780
ggaagaagtt ccgttttgct cccaccactt caacaagctc catctcaagg acgggaggtc    9840
cattgtggtt ccctgccgcc accaagatga actgattggc cgggcccgcg tctctccagg    9900
ggcgggatgg agcatccggg agactgcttg cctagcaaaa tcatatgcgc agatgtggca    9960
gctcctttat ttccacagaa gggacctccg actgatggcc aatgccattt gttcatctgt    10020
gccagttgac tgggttccaa ctgggagaac tacctggtca atccatggaa agggagaatg    10080
gatgaccact gaagacatgc ttgtggtgtg aacagagtg tggattgagg agaacgacca    10140
catggaagac aagaccccag ttacgaaatg gacagacatt ccctatttgg gaaaaggga    10200
agacttgtgg tgtggatctc tcataggggca cagaccgcgc accacctggg ctgagaacat    10260
taaaaacaca gtcaacatgg tgcgcaggat catagggtgat gaagaaaagt acatggacta    10320
cctatccacc caagttcgct acttgggtga agaagggtct acacctggag tgctgtaagc    10380
accaattta gtgttgtcag gcctgctagt cagccacagt ttggggaaag ctgtgcagcc    10440
tgtaaccccc ccaggagaag ctgggaaacc aagctcatag tcaggccgag aacgccatgg    10500
cacggaagaa gccatgctgc ctgtgagccc ctcagaggac actgagtcaa aaacccac    10560
gcgcttggaa gcgcaggatg ggaaagaag gtggcgacct tcccacccct tcaatctggg    10620
gcctgaactg gagactagct gtgaatctcc agcagaggga ctagtggtta gaggagaccc    10680
cccggaaaac gcaaaacagc atattgacgc tgggaaagac cagagactcc atgagtttcc    10740
accacgctgg ccgccaggca cagatcgccg aacagcggcg ccggtgtggg ggaaatccat    10800
ggtttct                                                              10807
```

<210> SEQ ID NO 3
<211> LENGTH: 10807
<212> TYPE: DNA
<213> ORGANISM: Artificial Sequence
<220> FEATURE:
<223> OTHER INFORMATION: Synthetic Genomic sequence of chimeric
ZIKVBR15-MC mutant miR4279 (10,807 nt)

<400> SEQUENCE: 3

| | | | | | |
|---|---|---|---|---|---|
| agttgttgat | ctgtgtgagt | cagactgcga | cagttcgagt | ctgaagcgag | agctaacaac | 60 |
| agtatcaaca | ggtttaattt | ggatttggaa | acgagagttt | ctggtcatga | aaacccaaa | 120 |
| aaagaaatcc | ggaggattcc | ggattgtcaa | tatgctaaaa | cgcggagtag | cccgtgtgag | 180 |
| cccctttggg | ggcttgaaga | ggctgccagc | cggacttctg | ctgggtcatg | gcccatcag | 240 |
| gatggtcttg | gcgattctag | cctttttgag | attcacggca | atcaagccat | cactgggtct | 300 |
| catcaataga | tgggggttcag | ttgggaaaaa | agaggctatg | gaaataataa | agaagttcaa | 360 |
| gaaagatctg | gctgccatgc | tgagaataat | caatgctagg | aaggagaaga | agagacgagg | 420 |
| cgcagatact | agtgtcggaa | ttgttggcct | cctgctgacc | acagctatgg | cagcggaggt | 480 |
| cactagacgt | gggagtgcat | actatatgta | cttggacaga | aacgatgctg | ggaggccat | 540 |
| atcttttcca | accacattgg | ggatgaataa | gtgttatata | cagatcatgg | atcttggaca | 600 |
| catgtgtgat | gccaccatga | gctatgaatg | ccctatgctg | gatgaggggg | tggaaccaga | 660 |
| tgacgtcgat | tgttggtgca | acacgacgtc | aacttgggtt | gtgtacggaa | cctgccatca | 720 |
| caaaaaggt | gaagcacgga | gatctagaag | agctgtgacg | ctcccctccc | attccactag | 780 |
| gaagctgcaa | acgcggtcgc | aaacctggtt | ggaatcaaga | gaatacacaa | agcacttgat | 840 |
| tagagtcgaa | aattggatat | tcaggaaccc | tggcttcgcg | ttagcagcag | ctgccatcgc | 900 |
| ttggcttttg | ggaagctcaa | cgagccaaaa | agtcatatac | ttggtcatga | tactgctgat | 960 |
| tgccccggca | tacagcatca | ggtgcatagg | agtcagcaat | agggactttg | tggaaggtat | 1020 |
| gtcaggtggg | acttgggttg | atgttgtctt | ggaacatgga | ggttgtgtca | ccgtaatggc | 1080 |
| acaggacaaa | ccgactgtcg | acatagagct | ggttacaaca | acagtcagca | acatggcgga | 1140 |
| ggtacgatcg | tactgctatg | aggcatcaat | atcagacatg | gcttcggaca | gccgctgccc | 1200 |
| aacacaaggt | gaagcctacc | ttgacaagca | atcagacact | caatatgtct | gcaaaagaac | 1260 |
| gttagtggac | agaggctggg | gaaatggatg | tggactttt | ggcaaaggga | gcctggtgac | 1320 |
| atgcgctaag | tttgcatgct | ccaagaaaat | gaccgggaag | agcatccagc | cagagaatct | 1380 |
| ggagtaccgg | ataatgctgt | cagttcatgg | ctcccagcac | agtgggatga | ctgtcaatga | 1440 |
| tataggatat | gaaactgatg | agaatagagc | gaaagttgag | ataacgccca | attcaccaag | 1500 |
| agccgaagcc | accctggggg | gttttggaag | cctaggactt | gattgtgaac | cgaggacagg | 1560 |
| ccttgacttt | tcagatttgt | attacttgac | tatgaataac | aagcactggt | tggttcacaa | 1620 |
| ggagtggttc | cacgacattc | cattaccttg | gcacgctggg | gcagacaccg | gaactccaca | 1680 |
| ctggaacaac | aaagaagcac | tggtagagtt | caaggacgca | catgccaaaa | ggcaaactgt | 1740 |
| cgtggttcta | gggagtcaag | aaggagcagt | tcacacggcc | cttgctggag | ctctggaggc | 1800 |
| tgagatggat | ggtgcaaagg | gaaggctgtc | ctctggccac | ttgaaatgtc | gcctgaaaat | 1860 |
| ggataaactt | agattgaagg | gcgtgtcata | ctccttgtgt | actgcagcgt | tcacattcac | 1920 |
| caagatcccg | gctgaaacac | tgcacgggac | agtcacagtg | gaggtacagt | acgcagggac | 1980 |
| agatggacct | tgcaaggttc | cagctcagat | ggcggtggac | atgcaaactc | tgaccccagt | 2040 |
| tgggaggttg | ataaccgcta | accccgtaat | cactgaaagc | actgagaact | ctaagatgat | 2100 |
| gctggaactt | gatccaccat | ttggggactc | ttacattgtc | ataggagtcg | gggagaagaa | 2160 |
| gatcacccac | cactggcaca | ggagtggcag | caccattgga | aaagcatttg | aggccactgt | 2220 |

```
gagaggcgcc aagagaatgg cagtcctggg ggacacagcc tgggactttg gatcagttgg      2280
aggcgctctc aactcattgg gcaagggcat ccatcaaatt tttggagcag ctttcaaatc      2340
attgtttgga ggaatgtcct ggttctcaca aattctcatt ggaacgttgc tgatgtggtt      2400
gggtctgaac acaaagaatg gatctatttc ccttatgtgc ttggccttag gggggtgtt      2460 gatcttctta tccacagccg tctctgctga tgtggggtgc tcggtggact tctcaaagaa      2520
ggagacgaga tgcggtacag gggtgttcgt ctataacgac gttgaagcct ggagggacag      2580
gtacaagtac catcctgact cccccgtag attggcagca gcagtcaagc aagcctggga       2640
agatggtatc tgcgggatct cctctgtttc aagaatggaa acatcatgt ggagatcagt       2700 agaaggggag ctcaacgcta tcctagagga gaatggagtt caactgacgg tcgttgtggg     2760
atctgtaaaa acccccatgt ggagaggtcc acagagattg cccgtgcctg tgaacgagct     2820
gccccacggc tggaaggctt gggggaaatc gtacttcgtc agagcagcaa agacaaataa   2880
cagctttgtc gtggatggtg acacactgaa ggaatgccca ctcaaacata gagcatggaa    2940
cagctttctt gtggaggatc atgggttcgg ggtatttcac actagtgtct ggctcaaggt     3000
tagagaagat tattcattag agtgtgatcc agccgttatt ggaacagctg ttaagggaaa    3060
ggaggctgta cacagtgatc taggctactg gattgagagt gagaagaatg acacatggag    3120
gctgaagagg gcccatctga tcgagatgaa acatgtgaa tggccaaagt cccacacatt     3180
gtggacagat ggaatagaag agagtgatct gatcataccc aagtctttag ctgggccact     3240
cagccatcac aataccagag agggctacag gacccaaatg aaagggccat ggcacagtga    3300
agagcttgaa attcggtttg aggaatgccc aggcactaag gtttacgtgg aggagacatg    3360
tggaacaaga ggaccatctc tgagatcaac cactgcaagc ggaagggtga tcgaggaatg    3420
gtgctgcagg gagtgcacaa tgcccccact gtcgttccgg gctaaagatg ctgttggta    3480 tggaatggag ataaggccca ggaaagaacc agaaagcaac ttagtaaggt caatggtgac    3540
tgcaggatca actgatcaca tggaccactt ctcccttgga gtgcttgtga tcctgctcat    3600
ggtgcaggaa gggctgaaga agagaatgac cacaaagatc atcataagca catcaatggc   3660
agtgctggta gctatgatcc tggaggatt ttcaatgagt gacctggcta agcttgcaat    3720
tttgatgggt gccaccttcg cggaaatgaa cactggagga gatgtagctc atctggcgct    3780
gatagcggca ttcaaagtca gaccagcgtt gctggtatct ttcatcttca gagctaattg   3840
gacaccccgt gaaagcatgc tgctggcctt ggcctcgtgt cttttgcaaa ctgcgatctc   3900
cgccttggaa ggcgacctga tggttctcat caatggtttt gctttggcct ggttggcaat   3960
acgagcgatg gttgttccac gcactgataa catcaccttg gcaatcctgg ctgctctgac   4020
accactggcc cggggcacac tgcttgtggc gtggagagca ggccttgcta cttgcggggg   4080
gtttatgctc ctctctctga agggaaaagg cagtgtgaag aagaacttac catttgtcat    4140
ggccctggga ctaaccgctg tgaggctggt cgaccccatc aacgtggtgg gactgctgtt   4200
actcacaagg agtgggaagc ggagctggcc ccctagcgaa gtactcacag ctgttggcct    4260
gatatgcgca ttggctggag ggttcgccaa ggcagatata gagatggctg gcccatggc    4320 cgcggtcggt ctgctaattg tcagttacgt ggtctcagga aagagtgtgg acatgtacat    4380
tgaaagagca ggtgacatca catgggaaaa agatgcggaa gtcactggaa acagtcccg    4440 gctcgatgtg cgctagatg agagtggtga tttctccctg gtggaggatg acggtccccc    4500
catgagagag atcatactca aggtggtcct gatgaccatc tgtggcatga atccaatagc    4560
catacccttt gcagctggag cgtggtacgt atacgtgaag actggaaaaa ggagtggtgc    4620
```

```
tctatgggat gtgcctgctc ccaaggaagt aaaaaagggg gagaccacag atggagtgta    4680
cagagtaatg actcgtagac tgctaggttc aacacaagtt ggagtgggag ttatgcaaga    4740
gggggtcttt cacactatgt ggcacgtcac aaaaggatcc gcgctgagaa gcggtgaagg    4800
gagacttgat ccatactggg gagatgtcaa gcaggatctg tgtcatact gtggtccatg     4860 gaagctagat gccgcctggg acgggcacag cgaggtgcag ctcttggccg tgccccccgg    4920
agagagagcg aggaacatcc agactctgcc cggaatattt aagacaaagg atggggacat    4980
tggagcggtt gcgctggatt acccagcagg aacttcagga tctccaatcc tagacaagtg    5040
tgggagagtg ataggacttt atggcaatgg ggtcgtgatc aaaaatggga gttatgttag    5100
tgccatcacc caagggaaga gggaggagga gactcctgtt gagtgcttcg agccctcgat    5160
gctgaagaag aagcagctaa ctgtcttaga cttgcatcct ggagctggga aaccaggag    5220 agttcttcct gaaatagtcc gtgaagccat aaaaacaaga ctccgtactg tgatcttagc    5280
tccaaccagg gttgtcgctg ctgaaatgga ggaggccctt agagggcttc cagtgcgtta    5340
tatgacaaca gcagtcaatg tcacccactc tggaacagaa atcgtcgact taatgtgcca    5400
tgccaccttc acttcacgtc tactacagcc aatcagagtc cccaactata atctgtatat    5460
tatggatgag gcccacttca cagatccctc aagtatagca gcaagaggat acatttcaac    5520
aagggttgag atgggcgagg cggctgccat cttcatgacc gccacgccac caggaacccg    5580
tgacgcattt ccggactcca actcaccaat tatggacacc gaagtggaag tcccagagag    5640
agcctggagc tcaggctttg attgggtgac ggatcattct ggaaaaacag tttggtttgt    5700
tccaagcgtg aggaacggca atgagatcgc agcttgtctg acaaaggctg gaaaacgggt    5760
catacagctc agcagaaaga cttttgagac agagttccag aaaacaaaac atcaagagtg    5820
ggactttgtc gtgacaactg acatttcaga tgggcgcc aactttaaag ctgaccgtgt     5880
catagattcc aggagatgcc taaagccggt catacttgat ggcgagagag tcattctggc    5940
tggacccatg cctgtcacac atgccagcgc tgctcagagg agagggcgca taggcaggaa    6000
tcccaacaaa cctggagatg agtatctgta tggaggtggg tgcgcagaga ctgacgaaga    6060
ccatgcacac tggcttgaag caagaatgct ccttgacaat atttacctcc aagatggcct    6120
catagcctcg ctctatcgac ctgaggccga caaagtagca gccattgagg gagagttcaa    6180
gcttaggacg gagcaaagga gacctttgt ggaactcatg aagagaggag accttcctgt     6240
ttggctggcc tatcaggttg catctgccgg aataacctac acagatagaa gatggtgctt    6300
tgatggcacg accaacaaca ccataatgga agatagtgtg ccggcagagg tgtggaccag    6360
acacggagag aaaagagtgc tcaaaccgag gtggatggac gccagagttt gttcagatca    6420
tgcggccctg aagtcattca aggagtttgc cgctgggaaa agaggagcgg cttttggagt    6480
gatggaagcc ctgggaacac tgccaggaca catgacagag agattccagg aagccattga    6540
caacctcgct gtgctcatgc gggcagagac tggaagcagg ccttacaaag ccgcggcggc    6600
ccaattgccg gagaccctag agaccataat gcttttgggg ttgctgggaa cagtctcgct    6660
gggaatcttc ttcgtcttga tgaggaacaa gggcataggg aagatgggct ttggaatggt    6720
gactcttggg gccagcgcat ggctcatgtg gctctcggaa attgagccag ccagaattgc    6780
atgtgtcctc attgttgtgt tcctattgct ggtggtgctc atacctgagc cagaaaagca    6840
aagatctccc caggacaacc aaatggcaat catcatcatg gtagcagtag gtcttctggg    6900
cttgattacc gccaatgaac tcggatggtt ggagagaaca aagagtgacc taagccatct    6960
aatgggaagg agagaggagg gggcaaccat aggattctca atggacattg acctgcggcc    7020
```

```
agcctcagct tgggccatct atgctgcctt gacaactttc attaccccag ccgtccaaca    7080
tgcagtgacc acttcataca acaactactc cttaatggcg atggccacgc aagctggagt    7140
gttgtttggt atgggcaaag ggatgccatt ctacgcatgg gactttggag tcccgctgct    7200
aatgataggt tgctactcac aattaacacc cctgaccctc atagtggcca tcattttgct    7260
cgtggcgcac tacatgtact tgatcccagg gctgcaggca gcagctgcgc gtgctgccca    7320 gaaagagaacg gcagctggca tcatgaagaa ccctgttgtg gatggaatag tggtgactga    7380
cattgacaca atgacaattg acccccaagt ggagaaaaag atgggacagg tgctactcat    7440
agcagtagcc gtctccagcg ccatactgtc gcggaccgcc tggggtgggg ggaggctgg    7500 ggccctgatc acagccgcaa cttccacttt gtgggaaggc tctccgaaca agtactggaa    7560
ctcctctaca gccacttcac tgtgtaacat ttttagggga agttacttgg ctggagcttc    7620
tctaatctac acagtaacaa gaaacgctgg cttggtcaag agacgtgggg gtggaacagg    7680
agagaccctg ggagagaaat ggaaggcccg cttgaaccag atgtcggccc tggagttcta    7740
ctcctacaaa aagtcaggca tcaccgaggt gtgcagagaa gaggcccgcc gcgccctcaa    7800
ggacggtgtg gcaacgggag gccatgctgt gtcccgagga agtgcaaagc tgagatggtt    7860
ggtggagcgg ggatacctgc agcccctatgg aaaggtcatt gatcttggat gtggcagagg    7920
gggctggagt tactacgccg ccaccatccg caaagttcaa gaagtgaaag gatacacaaa    7980
aggaggccct ggtcatgaag aacccgtgtt ggtgcaaagc tatgggtgga acatagtccg    8040
tcttaagagt ggggtggacg tctttcatat ggcggctgag ccgtgtgaca cgctgctgtg    8100
tgacataggt gagtcatcat ctagtcctga agtggaagaa gcacgacgc tcagagtcct    8160 ctccatggtg ggggattggc ttgaaaaaag accaggagcc ttttgtataa aagtgttgtg    8220
cccatacacc agcactatga tggaaaccct ggagcgactg cagcgtaggt atgggggagg    8280
actggtcaga gtgccactct cccgcaactc tacacatgag atgtactggg tctctggagc    8340
gaaaagcaac accataaaaa gtgtgtccac cacgagccag ctcctcttgg ggcgcatgga    8400
cgggcctagg aggccagtga atatgaggag ggatgtgaat ctcggctctg gcacgcgggc    8460
tgtggtaagc tgcgctgaag ctcccaacat gaagatcatt ggtaaccgca ttgaaaggat    8520
ccgcagtgag cacgcggaaa cgtggttctt tgacgagaac cacccatata ggacatgggc    8580
ttaccatgga agctatgagg cccccacaca agggtcagcg tcctctctaa taacgggt    8640 tgtcaggctc ctgtcaaaac cctgggatgt ggtgactgga gtcacaggaa tagccatgac    8700
cgacaccaca ccgtatggtc agcaaagagt tttcaaggaa aaagtggaca ctagggtgcc    8760 agaccccaa gaaggcactc gtcaggttat gagcatggtc tcttcctggt tgtggaaaga    8820
gctaggcaaa cacaaacggc cacgagtctg taccaaagaa gagttcatca acaaggttcg    8880
tagcaatgca gcattagggg caatatttga agaggaaaaa gagtggaaga ctgcagtgga    8940
agctgtgaac gatccaaggt tctgggctct agtggacaag gaaagagagc accacctgag    9000
aggagagtgc cagagttgtg tgtataacat gatgggaaaa agagaaaaga aacaagggga    9060
atttggaaag gccaagggca gccgcgccat ctggtatatg tggctagggg ctagatttct    9120
agagttcgaa gcccttggat tcttgaacga ggatcactgg atgggagag agaactcagg    9180 aggtggtgtt gaagggctgg gattacaaag actcggatat gtcctagaag agatgagtcg    9240
tataccagga ggaaggatgt atgcagatga cactgctggc tgggacaccc gcattagcag    9300
gtttgatctg gagaatgaag ctctaatcac caaccaaatg gagaaaggc acagggcctt    9360 ggcattggcc ataatcaagt acacatacca aaacaaagtg gtaaaggtcc ttagaccagc    9420
```

```
tgaaaaaggg aaaacagtta tggacattat ttcgagacaa gaccaaaggg ggagcggaca    9480
agttgtcact tacgctctta acacatttac caacctagtg gtgcaactca ttcggaatat    9540
ggaggctgag gaagttctag agatgcaaga cttgtggctg ctgcggaggt cagagaaagt    9600
gaccaactgg ttgcagagca acggatggga taggctcaaa cgaatggcag tcagtggaga    9660
tgattgcgtt gtgaagccaa ttgatgatag gtttgcacat gccctcaggt tcttgaatga    9720
tatgggaaaa gttagaaagg acacacaaga gtggaaaccc tcaactggat gggacaactg    9780
ggaagaagtt ccgttttgct cccaccactt caacaagctc catctcaagg acgggaggtc    9840
cattgtggtt ccctgccgcc accaagatga actgattggc cgggcccgcg tctctccagg    9900
ggcgggatgg agcatccggg agactgcttg cctagcaaaa tcatatgcgc agatgtggca    9960
gctcctttat ttccacagaa gggacctccg actgatggcc aatgccattt gttcatctgt   10020
gccagttgac tgggttccaa ctgggagaac tacctggtca atccatggaa agggagaatg   10080
gatgaccact gaagacatgc ttgtggtgtg gaacagagtg tggattgagg agaacgacca   10140 catgaagac aagaccccag ttacgaaatg gacagacatt ccctatttgg gaaaagggga   10200
agacttgtgg tgtggatctc tcatagggca cagaccgcgc accacctggg ctgagaacat   10260
taaaaacaca gtcaacatgg tgcgcaggat cataggtgat gaagaaaagt acatggacta   10320
cctatccacc caagttcgct acttgggtga agaagggtct acacctggag tgctgtaagc   10380
accaatttta gtgttgtcag gcctgctagt cagccacagt ttggggaaag ctgtgcagcc   10440
tgtaaccccc ccaggagaag ctgggaaacc aagctcatag tcaggccgag aacgccatgg   10500 cacgaagaa gccatgctgc ctgtgagccc ctcagaggac actgagtcaa aaacccccac   10560
gcgcttggaa gcgcaggatg ggaaaagaag gtggcgacct tccccaccct tcaatctggg   10620
gcctgaactg gagactagct gtgaatctcc agcagaggga ctagtggtta gaggagaccc   10680
cccggaaaac gcaaaacagc atattgacgc tgggaaagac cagagactcc atgagtttcc   10740
accacgctgg ccgccaggca cagatcgccg aacagcggcg ccggtgtggg ggaaatccat   10800
ggtttct                                                             10807

<210> SEQ ID NO 4
<211> LENGTH: 16
<212> TYPE: DNA
<213> ORGANISM: Artificial Sequence
<220> FEATURE:
<223> OTHER INFORMATION: Synthetic Sequence figure 1

<400> SEQUENCE: 4
ctatcctaga ggagaa                                                        16

<210> SEQ ID NO 5
<211> LENGTH: 15
<212> TYPE: DNA
<213> ORGANISM: Artificial Sequence
<220> FEATURE:
<223> OTHER INFORMATION: Synthetic sequence figure 1

<400> SEQUENCE: 5
tttacgtgga ggaga                                                         15

<210> SEQ ID NO 6
<211> LENGTH: 16
<212> TYPE: DNA
<213> ORGANISM: Artificial Sequence
<220> FEATURE:
<223> OTHER INFORMATION: Synthetic sequence figure 1
```

```
<400> SEQUENCE: 6
agagggagga ggagac                                                    16

<210> SEQ ID NO 7
<211> LENGTH: 16
<212> TYPE: DNA
<213> ORGANISM: Artificial Sequence
<220> FEATURE:
<223> OTHER INFORMATION: Synthetic sequence figure 1

<400> SEQUENCE: 7
gctgctcaga ggagag                                                    16

<210> SEQ ID NO 8
<211> LENGTH: 16
<212> TYPE: DNA
<213> ORGANISM: Artificial Sequence
<220> FEATURE:
<223> OTHER INFORMATION: Synthetic sequence figure 1

<400> SEQUENCE: 8
catgaagaga ggagac                                                    16

<210> SEQ ID NO 9
<211> LENGTH: 16
<212> TYPE: DNA
<213> ORGANISM: Artificial Sequence
<220> FEATURE:
<223> OTHER INFORMATION: Synthetic sequence figure 1

<400> SEQUENCE: 9
catgaagaga ggagac                                                    16
```